US006620950B2

(12) United States Patent
Holton et al.

(10) Patent No.: US 6,620,950 B2
(45) Date of Patent: Sep. 16, 2003

(54) METHOD FOR THE PREPARATION OF 1-DEOXY BACCATIN III, 1-DEOXY TAXOL AND 1-DEOXY TAXOL ANALOGS

(75) Inventors: Robert A. Holton, Tallahassee, FL (US); Suhan Tang, Edison, NJ (US); Feng Liang, Kenilworth, NJ (US); Carmen Somoza, Madrid (ES)

(73) Assignee: Florida State University, Tallahassee, FL (US)

( * ) Notice: Subject to any disclaimer, the term of this patent is extended or adjusted under 35 U.S.C. 154(b) by 0 days.

(21) Appl. No.: 10/236,798

(22) Filed: Sep. 6, 2002

(65) Prior Publication Data

US 2003/0028039 A1 Feb. 6, 2003

Related U.S. Application Data

(63) Continuation of application No. 08/850,942, filed on May 5, 1997, now Pat. No. 6,545,168.
(60) Provisional application No. 60/016,927, filed on May 6, 1996.

(51) Int. Cl.[7] .................. C07D 305/14; C07C 45/67
(52) U.S. Cl. .................. 549/510; 568/326; 568/338; 568/361
(58) Field of Search .................. 549/510; 568/326, 568/338, 361, 372, 375

(56) References Cited

U.S. PATENT DOCUMENTS

| | | | |
|---|---|---|---|
| 4,680,391 A | 7/1987 | Firestone et al. | |
| 4,814,470 A | 3/1989 | Colin et al. | |
| 4,857,653 A | 8/1989 | Colin et al. | |
| 4,876,399 A | 10/1989 | Holton et al. | |
| 4,924,011 A | 5/1990 | Denis et al. | |
| 4,924,012 A | 5/1990 | Colin et al. | |
| 4,942,184 A | 7/1990 | Haugwitz et al. | |
| 4,960,790 A | 10/1990 | Stella et al. | |
| 5,015,744 A | 5/1991 | Holton | |
| 5,059,699 A | 10/1991 | Kingston et al. | |
| 5,136,060 A | 8/1992 | Holton | |
| 5,175,315 A | 12/1992 | Holton | |
| 5,227,400 A | 7/1993 | Holton et al. | |
| 5,229,526 A | 7/1993 | Holton | |
| 5,243,045 A | 9/1993 | Holton et al. | |
| 5,250,683 A | 10/1993 | Holton et al. | |
| 5,254,703 A | 10/1993 | Holton | |
| 5,272,171 A | 12/1993 | Ueda et al. | |
| 5,274,124 A | 12/1993 | Holton | |
| 5,283,253 A | 2/1994 | Holton et al. | |
| 5,284,864 A | 2/1994 | Holton et al. | |
| 5,284,865 A | 2/1994 | Holton et al. | |
| 5,336,785 A | 8/1994 | Holton et al. | |
| 5,338,872 A | 8/1994 | Holton et al. | |
| 5,350,866 A | 9/1994 | Holton et al. | |
| 5,384,399 A | 1/1995 | Holton | |
| 5,399,726 A | 3/1995 | Holton et al. | |
| 5,430,160 A | 7/1995 | Holton | |
| 5,466,834 A | 11/1995 | Holton | |
| 5,481,010 A | 1/1996 | Ahond et al. | |
| 5,489,601 A | 2/1996 | Holton et al. | |
| 5,539,103 A | 7/1996 | Holton | |
| 5,587,489 A | 12/1996 | Holton et al. | |
| 5,654,447 A | 8/1997 | Holton et al. | |
| 5,717,115 A | 2/1998 | Holton et al. | |
| 5,723,634 A | 3/1998 | Holton et al. | |
| 5,728,850 A | 3/1998 | Holton et al. | |
| 5,760,219 A | 6/1998 | Holton et al. | |
| 5,990,325 A | 11/1999 | Holton et al. | |
| 6,066,747 A | 5/2000 | Holton et al. | |

FOREIGN PATENT DOCUMENTS

| | | |
|---|---|---|
| EP | 0247378 B1 | 12/1987 |
| EP | 0253738 A1 | 1/1988 |
| EP | 0253739 A1 | 1/1988 |
| EP | 0336840 A1 | 10/1989 |
| EP | 0336841 A1 | 10/1989 |
| EP | 0400971 A2 | 12/1990 |
| EP | 0428376 A1 | 5/1991 |
| EP | 0534707 B1 | 3/1993 |
| EP | 0534708 B1 | 3/1993 |
| EP | 0534709 A1 | 3/1993 |
| WO | WO 92/09589 A1 | 6/1992 |
| WO | WO 93/02065 A1 | 2/1993 |
| ZA | 919224 | 11/1990 |

OTHER PUBLICATIONS

Bartholomew, D. et al., "A Novel Rearrangement Reaction Conversion of 3–(chloromethyl)azetidin–2–ones to Azetidine–3–carboxylic Acid Esters", *Tetrahedron Letters*, 1991, pp. 4795–4798, vol. 32, No. 36.

Della Casa De Marcano, D.P. and Halsall, T.G., "Structures of Some Taxane Diterpenoids, Baccatins–III, –IV, –VI, and VII and 1–Dehydroxybaccatin–IV, Possessing an Oxetan Ring", *J. Chem. Soc., Chem. Commun.*, 1975, 365.

Denis, J. et al., "A Highly Efficient, Practical Approach to Natural Taxol", *J. Am. Chem. Soc.*, 1988, pp. 5917–5919, vol. 110, No. 17.

Denis, J. et al., "An Efficient, Enantioselective Synthesis of The Taxol Side Chain", *J. Org. Chem.*, 1986, pp. 46–50, vol. 51, No. 1.

Deutsch, H.M. et al., "Synthesis of Congeners and Prodrugs. 3.Water–Soluble Prodrugs of Taxol with Potent Antitumor-Activity", *Journal of Medicinal Chem.*, Apr. 1989, pp. 788–792, vol. 32, No. 4.

Holton, R. et al., "A Synthesis of Taxusin", *J. Am. Chem. Soc.*, 1988, pp. 6558–6560, 110.

Holton, R., "Synthesis of the Taxane Ring System", *Journal of theAmerican Chemical Society*, 1984, pp. 5731–5732, vol. 106.

Kaiser et al., "Synthesis of Esters of Acid–Unstable Alcohols by Means of n–butyllithium", *J. Org. Chem.*, 1970, 35, 1198.

(List continued on next page.)

*Primary Examiner*—Taofiq Solola
(74) *Attorney, Agent, or Firm*—Senniger, Powers, Leavitt & Roedel

(57) ABSTRACT

1-Deoxybaccatin III, 1-deoxytaxol and 1-deoxy taxol analogs and method for the preparation thereof.

2 Claims, No Drawings

OTHER PUBLICATIONS

Kingston, D. et al., "Progress in the Chemistry of Organic Natural Products", *Springer–Verlag,* 1993, pp. 1–206, New York.

Lian, J.–Y. Z.–Min, D., Mizuno, M., Tanaka, T., and Iinuma, M., "Two Taxane Diterpenes from *Taxus mairei*", *Phytochem.,* 1988, 27, 3674.

Magri, N. et al., "Modified Taxols, 4. Synthesis and Biological Activity of Taxols Modified in the Side Chain", *J. of Natural Products,* 1988, pp. 298–306, vol. 51, No. 2.

Min, Z.–D, Jiang, H., and Liang, J–Y., "Studies on the Taxane Diterpenes of the Heartwood from *Taxus mairei*",. *Acta Pharm. Sin* (*Yaoxue Xuebao*), 1989, 24, 673.

Mukerjee, A. et al., "β–Lactams: Retrospect and Prospect", *Tetrahedron,* 1978, pp. 1731–1767, vol. 34, Report No. 52.

Ojima, I. et al., "New and Efficient Approaches to the Semisynthesis of Taxol and its C–13 Side Chain Analogs by Means of β–Lactam Synthon Method", *Tetrahedron,* 1992, pp. 6985–7012, vol. 48, No. 34.

Samaranayake, G. et al., "Modified Taxols. 5. Reaction of Taxol With Electrophilic Reagents and Preparation of a Rearranged Taxol Derivative with Tubulin Assembly Activity", *J. Org. Chem.,* 1991, pp. 5114–5119, vol. 56.

Science/Technology, "New Family of Taxol, Taxotere Analogs Developed", *Chem. & Engineering News,* Apr. 12, 1993, pp. 26–27.

Schultz et al., "Synthesis of New N–radicals of Tetrazan–1–yl", *Chem. Abstr.,* 1998, pp. 581, vol. 108, No. 37298C.

Senilh et al., "Chime Organique Biologique—Hemisynthese de nouveaux analogues du taxol, Etude de leur interaction avec la tubuline", *C.R. Acad. Sc. Paris,* 1984, pp. 1039–1043, t. 299, Serie II, No. 15.

Wani, M. et al., "Plant Antitumor Agents. VI. The Isolation and Structure of Taxol, a Novel Antileukemic and Antitumor Agent from *Taxus brevifolia*", *J. Am. Chem. Soc.* 93:9, May 5, 1971, pp. 2325–2327.

Witherup, K. et al., "High Performance Liquid Chromatographic Separation of Taxol and Related Compounds From *Taxus brevifolia*", *Jor. of Liquid Chromatography,* 1989, pp. 2117–2132, 12(11).

Zhang, Z. et al., "Taxanes from *Taxus yunnanesis*", *Phytochemistry,* 1990, pp. 3673–3675, vol. 29, No. 11.

METHOD FOR THE PREPARATION OF 1-DEOXY BACCATIN III, 1-DEOXY TAXOL AND 1-DEOXY TAXOL ANALOGS

REFERENCE TO RELATED APPLICATION

This application is a continuation application based on U.S. Ser. No. 08/850,942, filed May 5, 1997, now U.S. Pat. No. 6,545,168 which claims priority, at least in part, from Provisional Application Ser. No. 60/016,927, filed May 6, 1996.

This invention was made with Government support under NIH Grant #CA 42031 awarded by the National Institutes of Health. The Government has certain rights in the invention.

BACKGROUND OF THE INVENTION

The present invention is directed to novel taxanes which have utility as antitumor agents and to a process for their preparation.

The taxane family of terpenes, of which baccatin III and taxol are members, has attracted considerable interest in both the biological and chemical arts. Taxol is a promising cancer chemotherapeutic agent with a broad spectrum of tumor-inhibiting activity. Taxol has a 2'R, 3'S configuration and the following structural formula:

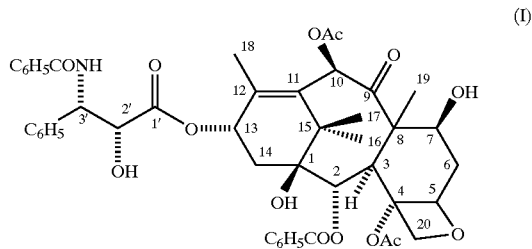

(I)

wherein Ac is acetyl. Because of this promising activity, taxol is currently undergoing clinical trials in both France and the United States.

Colin et al. reported in U.S. Pat. No. 4,814,470 that taxol derivatives having the structural formula (II) below, have an activity significantly greater than that of taxol (I).

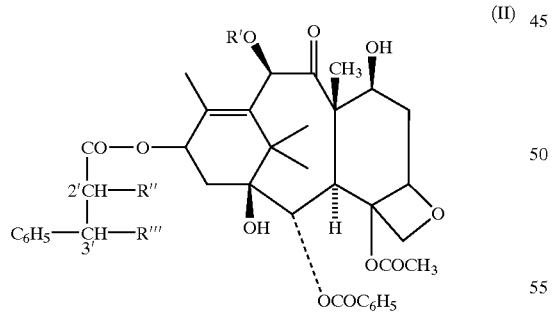

(II)

R' represents hydrogen or acetyl and one of R" and R'" represents hydroxy and the other represents tert-butoxycarbonylamino and their stereoisomeric forms, and mixtures thereof. The compound of this formula in which R" is hydroxy, R'" is tert-butoxycarbonylamino having the 2'R, 3'S configuration is commonly referred to as taxotere.

Although taxol and taxotere are promising chemotherapeutic agents, they are not universally effective. Accordingly, a need remains for additional chemotherapeutic agents.

SUMMARY OF THE INVENTION

Among the objects of the present invention, therefore, is the provision of novel taxanes which are valuable anti-tumor agents and a process for their preparation.

Briefly, therefore, the present invention is directed to a process for the preparation of 1-deoxy baccatin III, 1-deoxy taxol and 1-deoxy taxol analogs. The process comprises at least one of the following steps:

(a) reacting a compound having the formula:

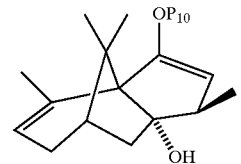

[3]

with a peracid such as metachloroperbenzoic acid to form a compound having the formula:

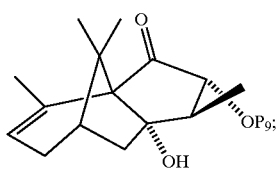

[4]

wherein $P_{10}$ is a silyl hydroxy protecting group such as triethylsilyl or an acyl group such as benzoyl. In this reaction, the protected hydroxy group —$OP_{10}$ migrates to the adjacent carbon and becomes —$OP_9$ with $P_9$ being the same as $P_{10}$;

(b) subjecting a compound having the formula:

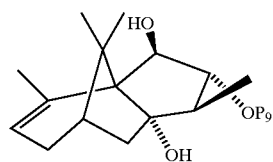

[5]

to an epoxy alcohol fragmentation consisting of (ia) epoxidation of an olefinic residue with a hydroperoxide, preferably t-BuOOH, in the presence of a transition metal catalyst, preferably titanium tetraisopropoxide, or (ib) treatment of the olefinic residue with a peracid such as peracetic acid followed by (ii) addition of a sulfide, preferably dimethyl sulfide, followed by heating in the presence of a transition metal catalyst, preferably titanium tetraisopropoxide, to form a compound having the formula:

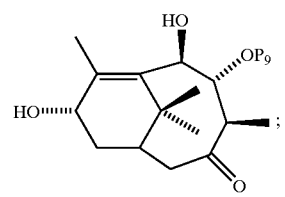

[6]

wherein $P_9$ is a hydroxyl protecting group such as a silyl group, ketal, acetal, or ether which does not contain a reactive functionality;

(c) reacting a compound having the formula:

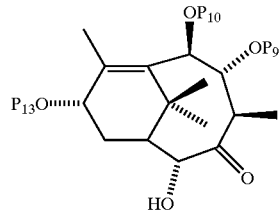

[9]

with a vinyl organometallic reagent to form a compound having the formula:

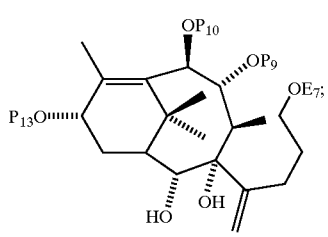

[10]

(d) reacting a compound having the formula:

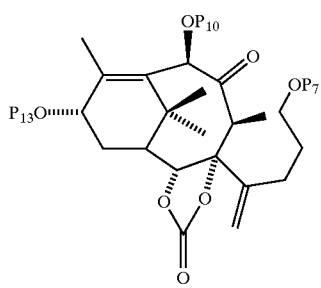

[14]

with a palladium catalyst to form a compound having the formula:

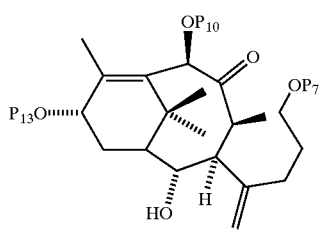

[15]

(e) reacting a compound having the formula:

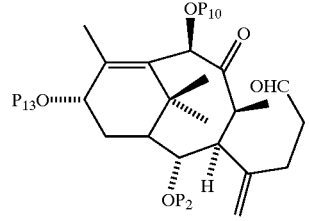

[17]

with a base, most preferably BaO in methanol, and protecting the C7 hydroxy substituent, for example, by reacting the product with TESOTf, to form a compound having the formula:

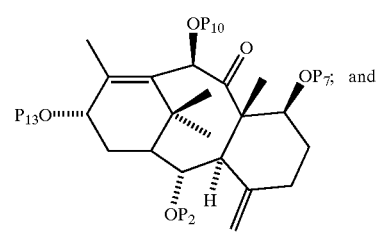

[18]

(f) reacting a compound having the formula:

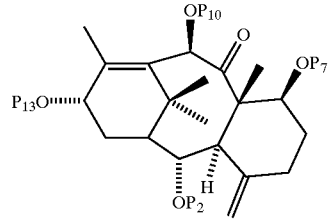

[18]

with $SeO_2$ to form a compound having the formula:

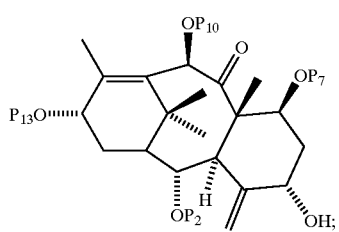

[19]

wherein $E_7$ is hydrogen or a hydroxy protecting group, and $P_2$, $P_7$, $P_9$, $P_{10}$ and $P_{13}$ are hydroxy protecting groups as hereinafter defined.

In general, the process of the present invention may be used to prepare 1-deoxy baccatin III, 1-deoxy taxol and 1-deoxy taxol analogs having the formula:

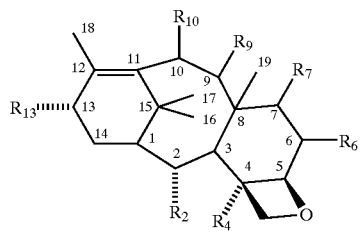

wherein

M comprises ammonium or is a metal;

$R_2$ is —$OT_2$, —$OCOZ_2$, or —$OCOOZ_2$;

$R_4$ is —$OT_4$, —$OCOZ_4$, or —$OCOOZ_4$;

$R_6$ is hydrogen, keto, —$OT_6$, —$OCOZ_6$ or —$OCOOZ_6$;

$R_7$ is hydrogen, halogen, —$OT_7$, —$OCOZ_7$ or —$OCOOZ_7$;

$R_9$ is hydrogen, keto, —$OT_9$, —$OCOZ_9$ or —$OCOOZ_9$;

$R_{10}$ is hydrogen, keto, —$OT_{10}$, —$OCOZ_{10}$ or —$OCOOZ_{10}$;

$R_6$, $R_7$, $R_9$, and $R_{10}$ independently have the alpha or beta stereochemical configuration;

$R_{13}$ is hydroxy, protected hydroxy, keto, MO— or

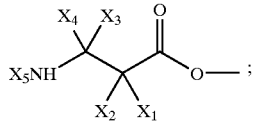

$T_2$, $T_4$, $T_6$, $T_7$, $T_9$ and $T_{10}$ are independently hydrogen or hydroxy protecting group;

$X_1$ is —$OX_6$;

$X_2$ is hydrogen, hydrocarbon, heterosubstituted hydrocarbon, or heteroaryl;

$X_3$ and $X_4$ are independently hydrogen, hydrocarbon, heterosubstituted hydrocarbon, or heteroaryl;

$X_5$ is —$COX_{10}$, —$COOX_{10}$, —$COSX_{10}$, or —$CONX_8X_{10}$;

$X_6$ is hydrogen, hydrocarbon, heterosubstituted hydrocarbon, heteroaryl, or hydroxy protecting group or a functional group which increases the water solubility of the taxane derivative;

$X_8$ is hydrogen, hydrocarbon, heterosubstituted hydrocarbon;

$X_{10}$ is hydrocarbon, heterosubstituted hydrocarbon, or heteroaryl; and $Z_2$, $Z_4$, $Z_6$, $Z_7$, $Z_9$ and $Z_{10}$ are independently hydrocarbon, heterosubstituted hydrocarbon, or heteroaryl.

The present invention is additionally directed to compounds having the formulae

[2]

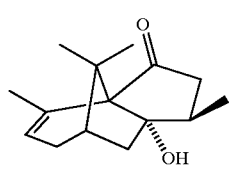

[3]

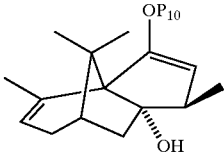

[4]

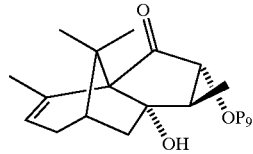

[5]

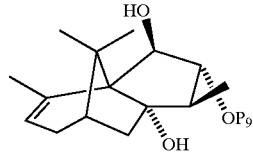

[6]

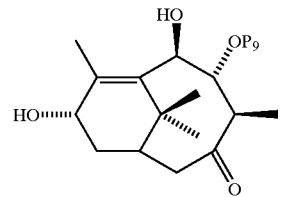

[7]

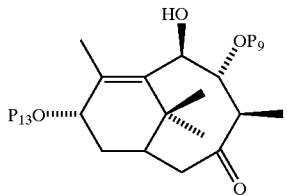

[8]

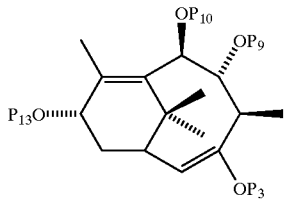

[9]

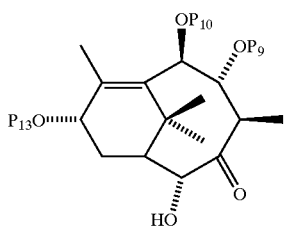

[10]

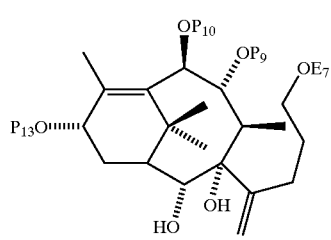

[11]
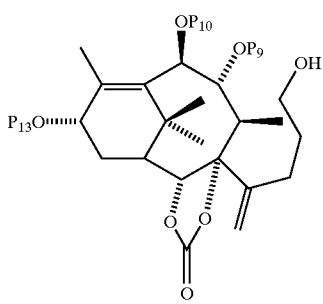
[12]
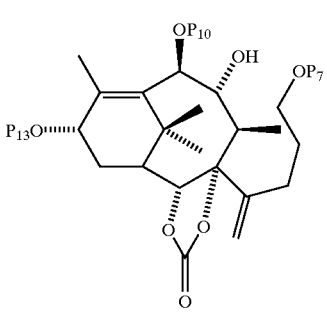
[13]
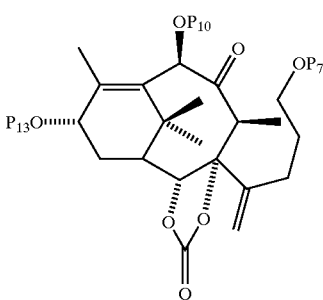
[14]
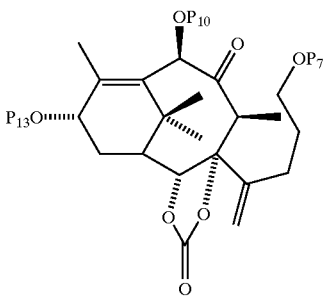
[15]
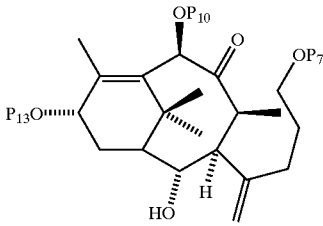
[16]
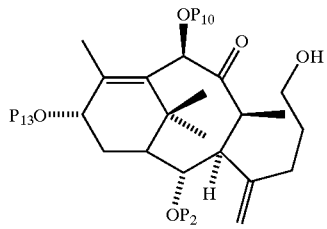
[17]
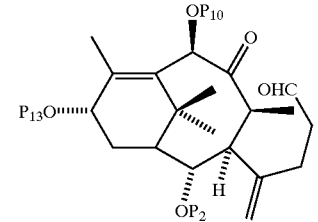
[18]
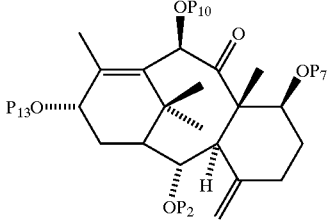
[19]
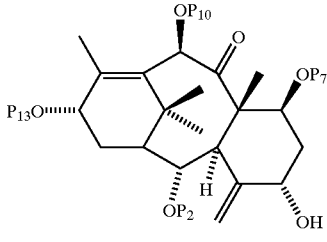
[20]
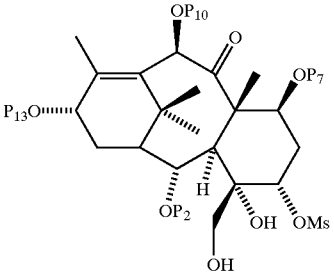
[21]
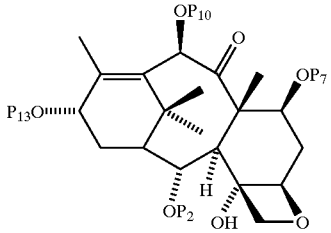

9

-continued

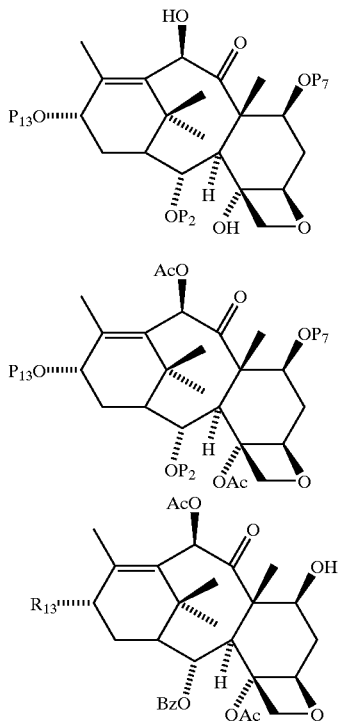

wherein $E_7$ is hydrogen or a hydroxy protecting group; Bz is benzoyl; $P_2, P_3, P_7, P_9, P_{10}$ and $P_{13}$ are hydroxy protecting groups; and $R_{13}$ is as previously defined. These compounds are key intermediates in the synthesis of 1-deoxy baccatin III, 1-deoxy taxol and other analogs. The present invention is also directed to processes for the preparation of these key intermediates.

Other objects and features of this invention will be in part apparent and in part pointed out hereinafter.

DETAILED DESCRIPTION OF THE PREFERRED EMBODIMENTS

The process of the present invention enables the preparation of 1-deoxy taxol, 1-deoxy taxotere and analogs of 1-deoxy taxol and 1-deoxy taxotere from 1-deoxy baccatin III, 1-deoxy-10-deactylbaccatin III, or analogs thereof. In a preferred embodiment, these compounds have the formula:

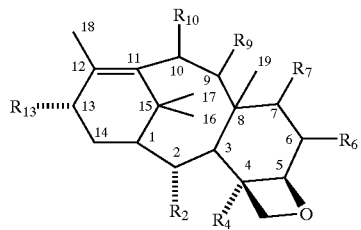

wherein

M comprises ammonium or is a metal;

$R_2$ is —$OCOZ_2$;

$R_4$ is —$OCOZ_4$;

$R_6$ is hydrogen;

10

$R_7$ is hydrogen, —$OT_7$, or —$OCOZ_7$;

$R_9$ is hydrogen, keto, —$OT_9$, —$OCOZ_9$;

$R_{10}$ is hydrogen, keto, —$OT_{10}$, or —$OCOZ_{10}$;

$R_{13}$ is MO— or

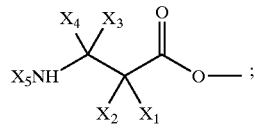

$T_7, T_9$ and $T_{10}$ are independently hydrogen or hydroxy protecting group;

$X_1$ is —$OX_6$;

$X_2$ is hydrogen;

$X_3$ is alkyl, substituted alkyl, alkenyl, substituted alkenyl, alkynyl, substituted alkynyl, aryl, substituted aryl, or heteroaryl;

$X_4$ is hydrogen;

$X_5$ is —$COX_{10}$ or —$COOX_{10}$;

$X_6$ is hydrogen or hydroxy protecting group;

$X_{10}$ is alkyl, substituted alkyl, alkenyl, substituted alkenyl, alkynyl, substituted alkynyl, phenyl, substituted phenyl, or heteroaryl; and $Z_2$ is alkyl, substituted alkyl, phenyl, substituted phenyl, or heteroaryl;

$Z_4$ is phenyl, substituted phenyl, or heteroaryl; and $Z_7, Z_9$ and $Z_{10}$ are independently alkyl, substituted alkyl, phenyl, substituted phenyl, or heteroaryl.

An exemplary synthesis of 1-deoxy baccatin III is depicted in Reaction Scheme 1. The starting material, diol 1, can be prepared from patchino (commonly known as B-patchouline epoxide) which is commercially available. The patchino is first reacted with an organo-metallic, such as lithium t-butyl followed by oxidation with an organic peroxide, such as t-butylperoxide in the presence of titanium tetraisopropoxide to form a tertiary alcohol. The tertiary alcohol is then reacted with a Lewis acid, such as boron trifluoride at low temperature, in the range from 40° C. to –100° C.; in the presence of an acid, such as trifluoromethane sulfonic acid. A graphical depiction of this reaction scheme along with an experimental write-up for the preparation of diol 1 can be found in U.S. Pat. No. 4,876,399.

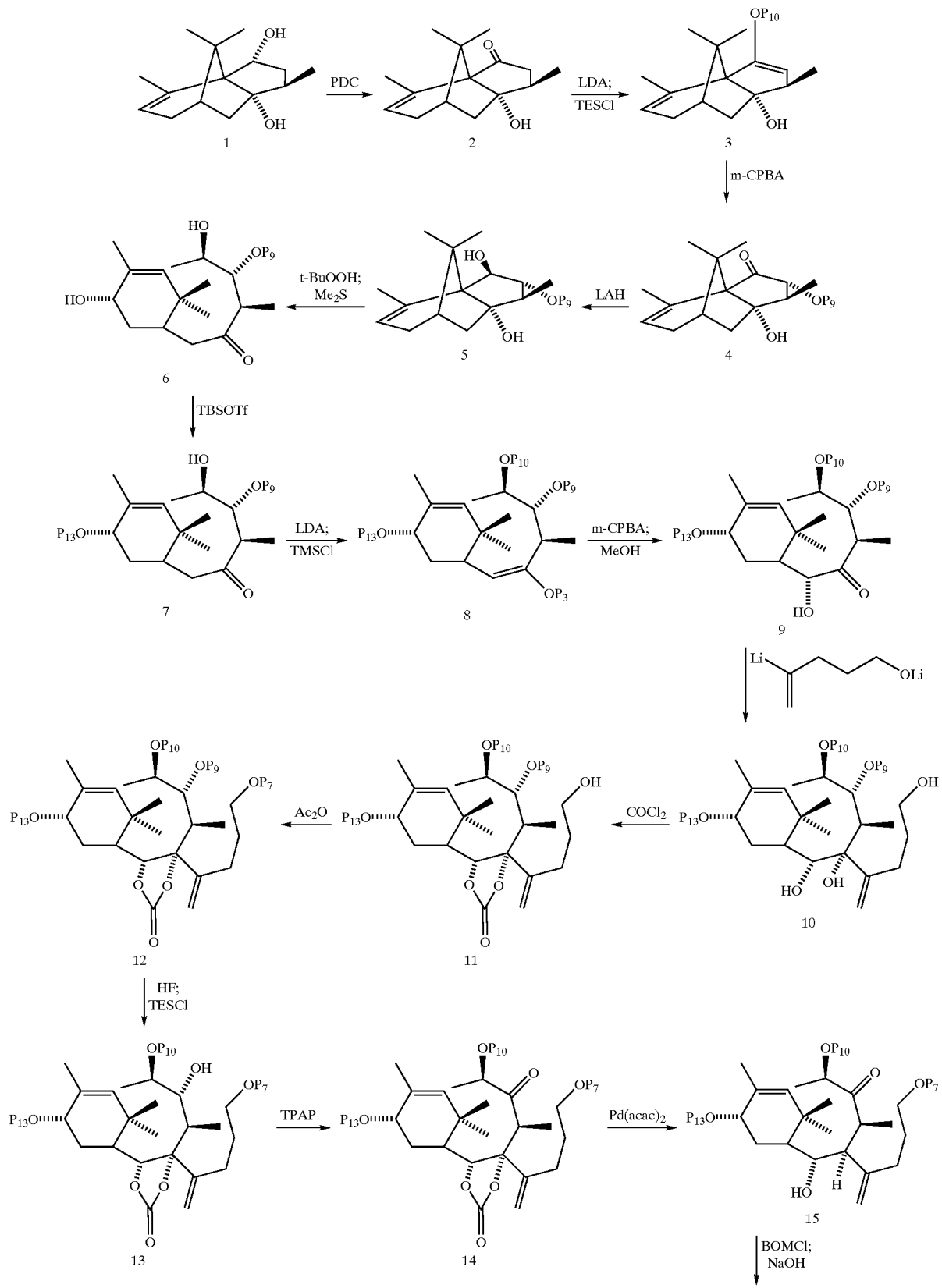
REACTION SCHEME 1

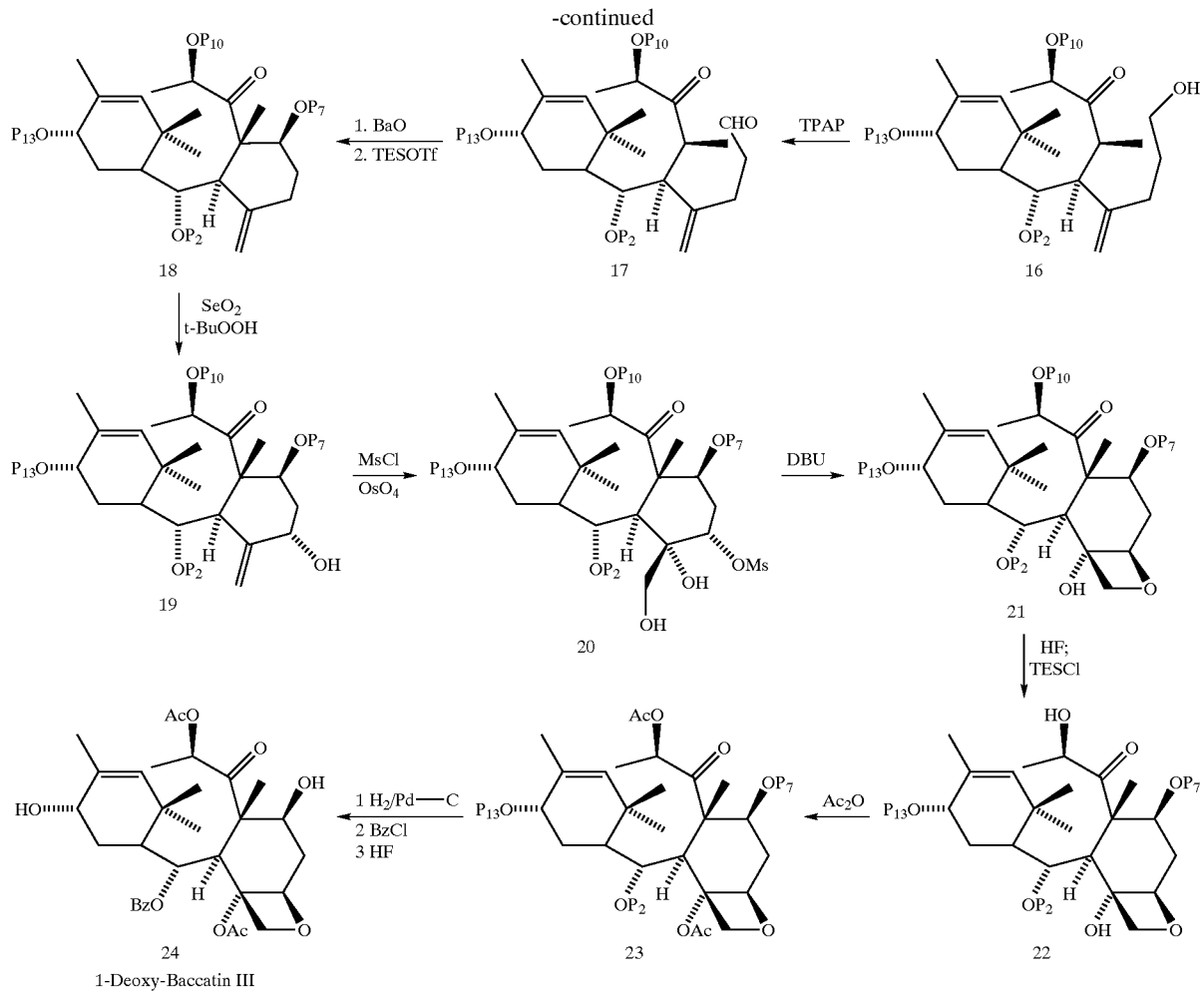

In this reaction scheme, $P_2$ is BOM; $P_3$ is TMS; $P_7$ is Ac in compounds 12–15 and TES in compounds 18–23; $P_9$ is TES in compounds 4, 5, 6 and 7, and TMS in compounds 8, 9, 10, 11 and 12; $P_{10}$ is TES, and $P_{13}$ is TBS in compounds 7 through 21 and TES in compounds 22 and 23. It should be understood, however, that $P_2$, $P_3$, $P_7$, $P_9$, $P_{10}$, and $P_{13}$ may be other hydroxy protecting groups.

In general, tetracyclic taxanes bearing C13 side chains may be obtained by reacting a β-lactam with alkoxides having the taxane tetracyclic nucleus and a C-13 metallic or ammonium oxide substituent to form compounds having a β-amido ester substituent at C-13. The β-lactams have the following structural formula:

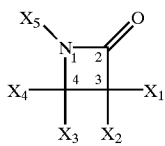

wherein $X_1$–$X_5$ are as defined above. The alkoxides having the tetracyclic taxane nucleus and a C-13 metallic oxide or ammonium oxide substituent have the following structural formula:

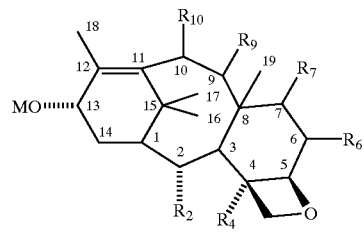

wherein $R_2$, $R_4$, $R_6$, $R_7$, $R_9$, $R_{10}$ and $R_{13}$ are as previously defined and M comprises ammonium or is a metal optionally selected from Group IA, IIA, transition (including lanthanides and actinides), IIB, IIIA, IVA, VA, or VIA metals (CAS version). If M comprises ammonium, it is preferably tetraalkylammonium and the alkyl component of the tetraalkylammonium substituent is preferably $C_1$–$C_{10}$ alkyl such as methyl or butyl.

1-Deoxytaxol may be prepared by protecting the C7 hydroxy group of 1-deoxy Baccatin III 24 with a suitable hydroxy protecting group, converting the 7-protected Baccatin III to the corresponding alkoxide and reacting the alkoxide with a β-lactam in which $X_1$ is protected hydroxy, $X_3$ is phenyl, $X_5$ is benzoyl and $X_2$ and $X_4$ are hydrogen. Protecting groups such as 2-methoxypropyl ("MOP"), 1-ethoxyethyl ("EE"), benzyloxymethyl are preferred, but a variety of other standard protecting groups such as trialkyl and triaryl silyl groups may be used.

1-Deoxytaxotere may be prepared in the same manner as 1-deoxytaxol except that 1-deoxy-10-deacetylbaccatin III is used instead of 1-deoxybaccatin III and $X_5$ of the β-lactam is t-butoxycarbonyl instead of benzoyl. 1-deoxy-10-deacetyl-baccatin III may be prepared as set forth in Reaction Scheme 2, starting with compound 22.

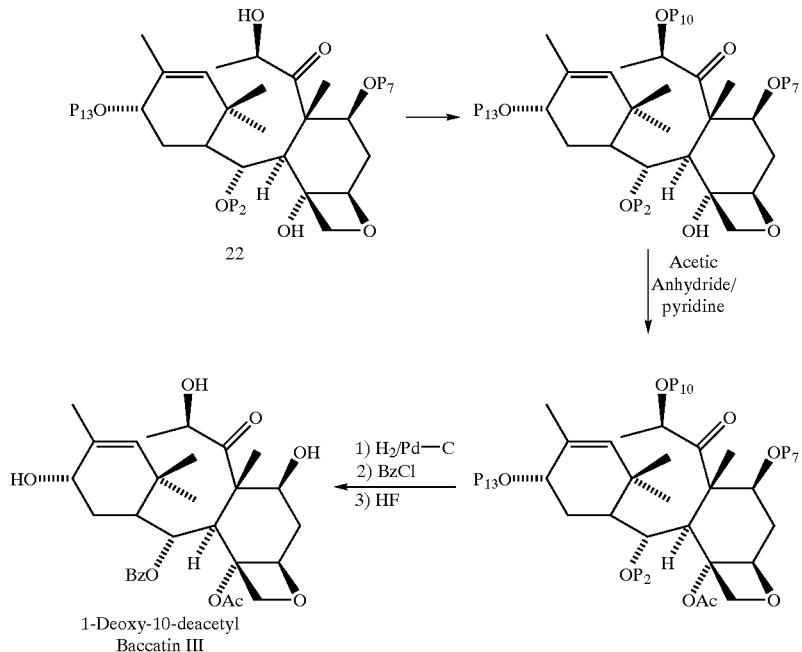

Analogs of 1-deoxy taxol and 1-deoxytaxotere bearing alternative side chain substituents may be prepared by using other suitably substituted β-lactams. For example, 1-deoxy taxol and 1-deoxytaxotere analogs having alkyl, alkenyl, alkynyl, substituted aryl, heteroaryl or substituted heteroaryl substituents at the C3' position are prepared using β-lactams in which $X_3$ is alkyl, alkenyl, alkynyl, substituted aryl, heteroaryl or substituted heteroaryl. Alternatively, $X_5$ of the β-lactam may be $-COX_{10}$, $-COOX_{10}$, $-COSX_{10}$ or $-CONX_8X_{10}$ wherein $X_8$ and $X_{10}$ are as previously defined.

1-deoxy-10-desacetoxy analogs of taxol can be prepared from the corresponding 1-deoxy-10-desacetoxy derivatives of baccatin III and 1-deoxy-10-desoxy derivatives of 10-DAB. These derivatives may be prepared as illustrated in Reaction Scheme 3 by reacting 1-deoxy-baccatin III or 1-deoxy-10-DAB (or their derivatives) with samarium diiodide. Reaction between the tetracyclic taxane having a C10 leaving group and samarium diiodide may be carried out at 0° C. in a solvent such as tetrahydrofuran. Advantageously, the samarium diiodide selectively abstracts the C10 leaving group; C13 side chains and other substituents on the tetracyclic nucleus remain undisturbed.

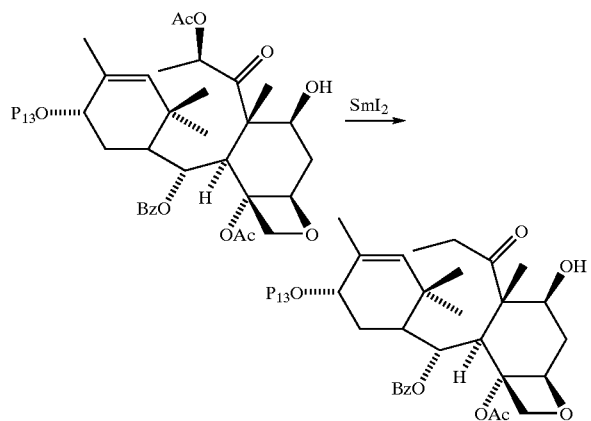

Analogs of 1-deoxy taxol and 1-deoxytaxotere having alternative C9 substituents may be prepared by selectively reducing the C9 keto substituent of 1-deoxytaxol, 1-deoxy-10-DAB, 1-deoxybaccatin III or one of the other intermediates disclosed herein to yield the corresponding 9-β-hydroxy-1-deoxy derivative. The reducing agent is preferably a borohydride and, most preferably, tetrabutylammoniumboro-hydride ($Bu_4NBH_4$) or triacetoxyborohydride.

As illustrated in Reaction Scheme 4, the reaction of 1-deoxybaccatin III 24 with $Bu_4NBH_4$ in methylene chloride yields 9-desoxo-9β-hydroxy-1-deoxybaccatin III 25.

After the C7 hydroxy group is protected with a suitable protecting group, a suitable side chain may be attached to 7-protected-9β-hydroxy-1-deoxy derivative 26 as elsewhere described herein. Removal of the remaining protecting groups thus yields 9β-hydroxy-desoxo-1-deoxy taxol or other 9-β-hydroxy-1-deoxytetracylic taxane having a C13 side chain.

REACTION SCHEME 4

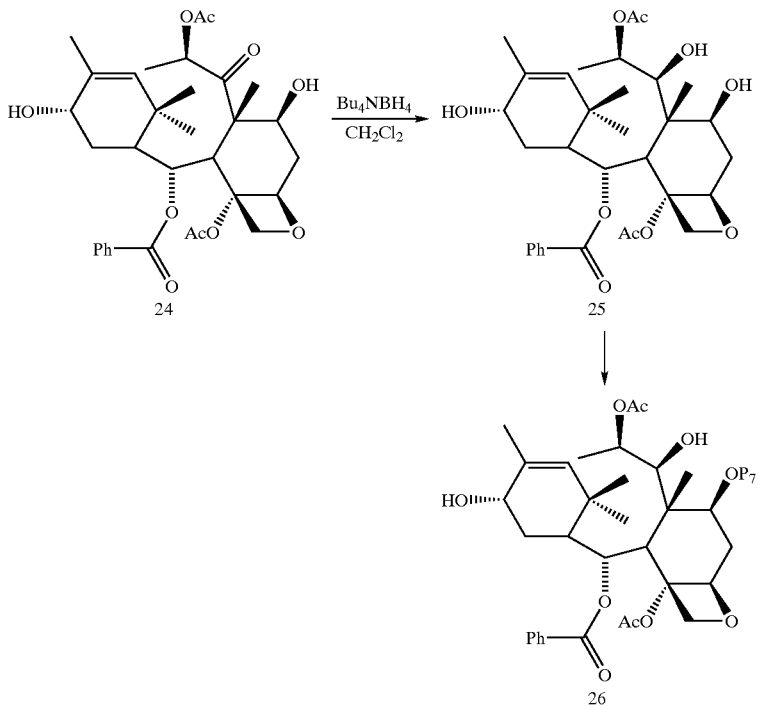

Alternatively, the C13 hydroxy group of 7-protected-9β-hydroxy-1-deoxy derivative 26 may be protected with a protecting group which can be selectively removed relative to the C7 hydroxy protecting group as illustrated in Reaction Scheme 5, to enable further selective manipulation of the various substituents of the taxane. For example, reaction of 7,13-protected-9β-hydroxy-1-deoxy derivative 27 with KH causes the acetate group to migrate from C10 to C9 and the hydroxy group to migrate from C9 to C10, thereby yielding 10-desacetyl derivative 28. Protection of the C10 hydroxy group of 10-desacetyl derivative 28 with a protecting group yields derivative 29. Selective removal of the C13 hydroxy protecting group from derivative 29 yields derivative 30 to which a suitable side chain may be attached as described above.

REACTION SCHEME 5

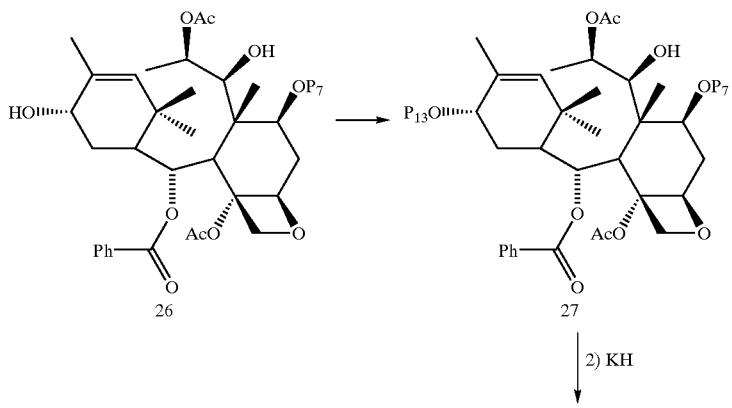

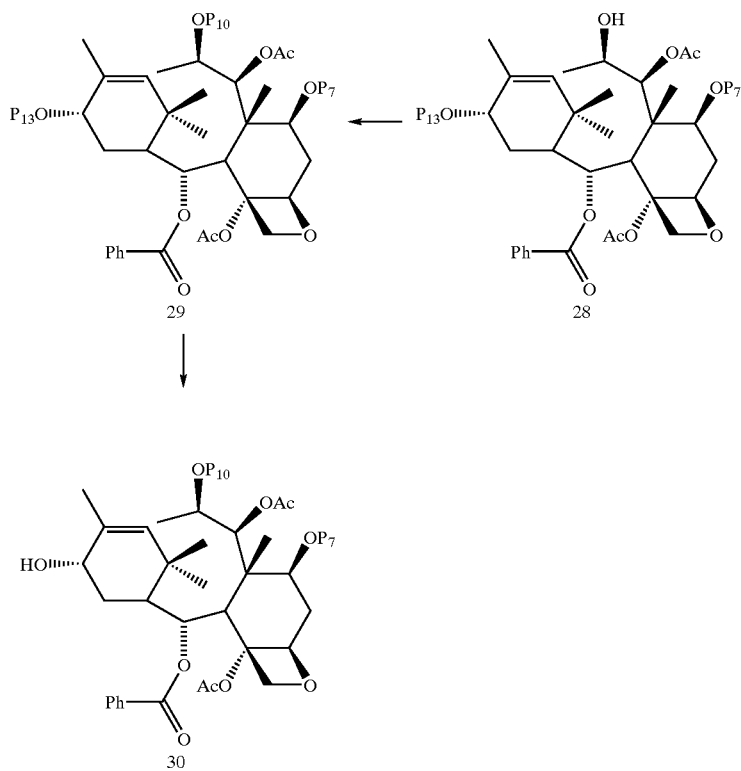

As shown in Reaction Scheme 6, 10-oxo derivative 31 can be provided by oxidation of 10-desacetyl derivative 28. Thereafter, the C13 hydroxy protecting group can be selectively removed followed by attachment of a side chain as described above to yield 9-acetoxy-10-oxo-taxol or other 9-acetoxy-10-oxotetracylic taxanes having a C13 side chain. Alternatively, the C9 acetate group can be selectively removed by reduction of 10-oxo derivative 31 with a reducing agent such as samarium diiodide to yield 9-desoxo-10-oxo derivative 32 from which the C13 hydroxy protecting group can be selectively removed followed by attachment of a side chain as described above to yield 9-desoxo-10-oxo-1-deoxytaxol or other 9-desoxo-10-oxo-1-deoxytetracylic taxanes having a C13 side chain.

REACTION SCHEME 6

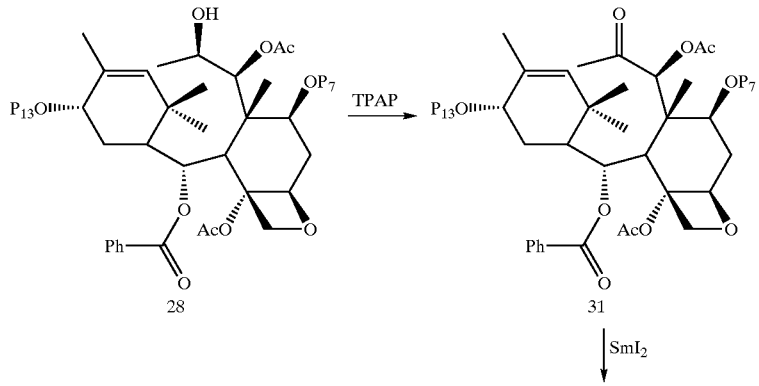

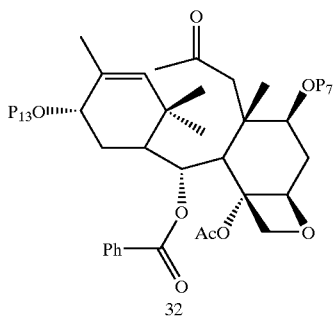

Reaction Scheme 7 illustrates a reaction in which 1-deoxy-10-DAB is reduced to yield tetraol 33. The C7 and C10 hydroxyl groups of tetraol 33 can then be selectively protected with a protecting group to produce diol 34 to which a C13 side chain can be attached as described above or, alternatively, after further modification of the tetracylic substituents.

1-deoxy-10-DAB 35 may then be readily acylated with any standard acylating agent such as an acid chloride to yield derivative 36 having a new C10 acyloxy substituent. Use of the analogous chloroformate instead of the acid chloride would yield the corresponding carbonate. Deprotection of the C7 hydroxy group, followed by selective reduction of the

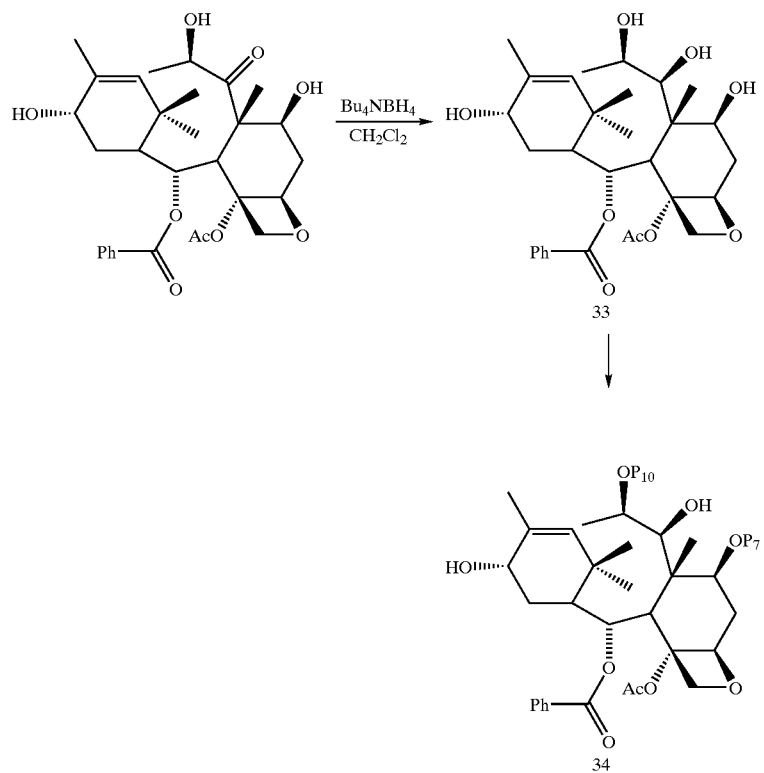

REACTION SCHEME 7

Taxanes having C9 and/or C10 acyloxy substituents other than acetoxy can be prepared using 1-deoxy-10-DAB as a starting material as illustrated in Reaction Scheme 8. After protecting the C7 hydroxy of 1-deoxy-10-DAB with a suitable protecting group to yield 7-protected 1-deoxy-10-DAB 35, the C10 hydroxy substituent of 7-protected C9 keto substituent of derivative 36 with tetrabutylammonium borohydride, and then protection of the C7 hydroxy group yields 9β-hydroxy derivative 37 to which a C13 side chain may be attached. Alternatively, the C10 and C9 groups can be caused to migrate as set forth in Reaction Scheme 5, above.

REACTION SCHEME 8

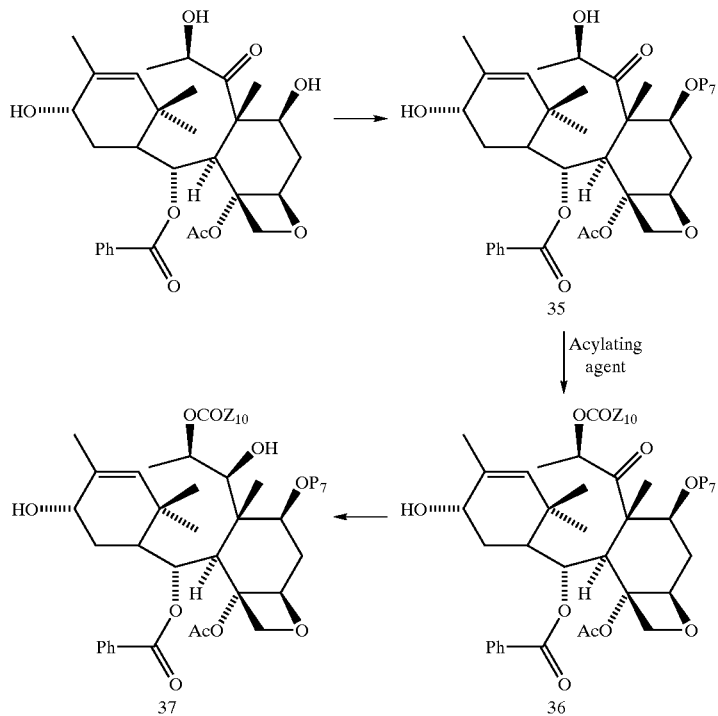

Taxanes having alternative C2 and/or C4 esters can be prepared using baccatin III and 10-DAB as starting materials. The C2 and/or C4 esters of baccatin III and 10-DAB can be selectively reduced to the corresponding alcohol(s) using reducing agents such as LAH or Red-Al, and new esters can thereafter be substituted using standard acylating agents such as anhydrides and acid chlorides in combination with an amine such as pyridine, triethylamine, DMAP, or diisopropyl ethyl amine. Alternatively, the C2 and/or C4 alcohols may be converted to new C2 and/or C4 esters through formation of the corresponding alkoxide by treatment of the alcohol with a suitable base such as LDA followed by an acylating agent such as an acid chloride. See, e.g., U.S. Pat. No. 5,399,726 which is incorporated herein by reference with respect to the preparation of taxanes having different C2 and C4 acyloxy substituents.

In Reaction Scheme 9, 7,10,13-protected 10-DAB 38 is converted to the diol 39 with lithium aluminum hydride. Deprotonation of diol 39 with LDA followed by reaction with an acid chloride selectively gives the C2 ester 40. Deprotonation of the C2 ester 40 with LDA followed by reaction with acid chloride gives the C2, C4 ester 41. If a chloroformate is used instead of the acid chloride, the product is a C2 or C4 carbonate (—$OCOOZ_2$ or —$OCOOZ_4$).

REACTION SCHEME 9

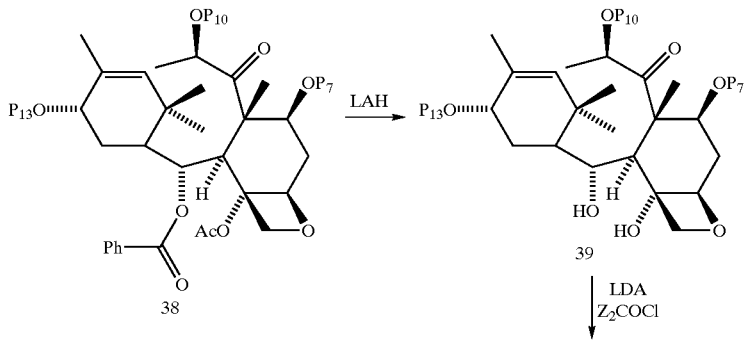

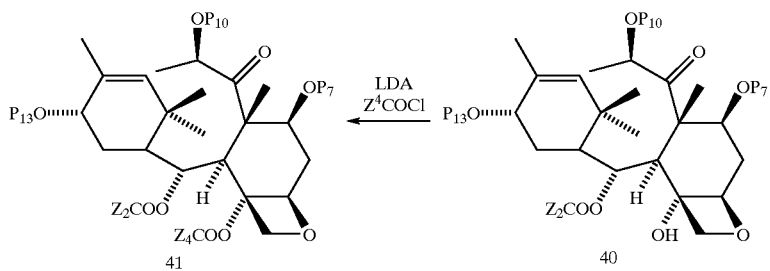
C7 dihydro and other C7 substituted taxanes can be prepared as set forth in Reaction Schemes 10, 11 and 12.
REACTION SCHEME 10
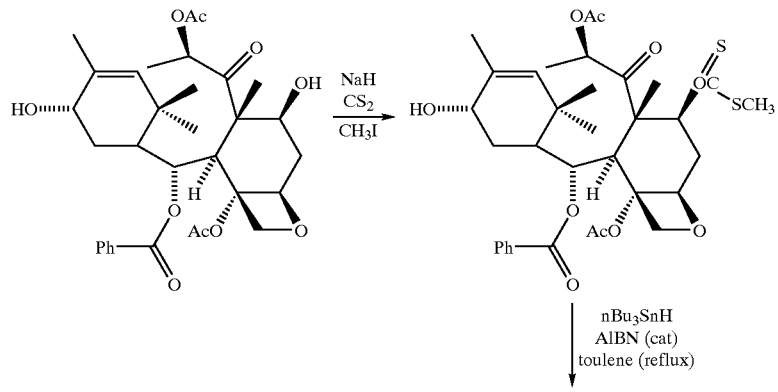
REACTION SCHEME 11
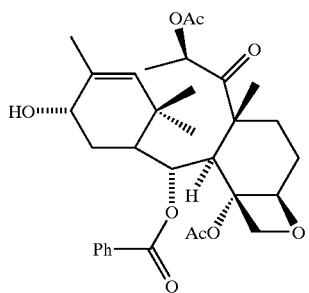
-continued
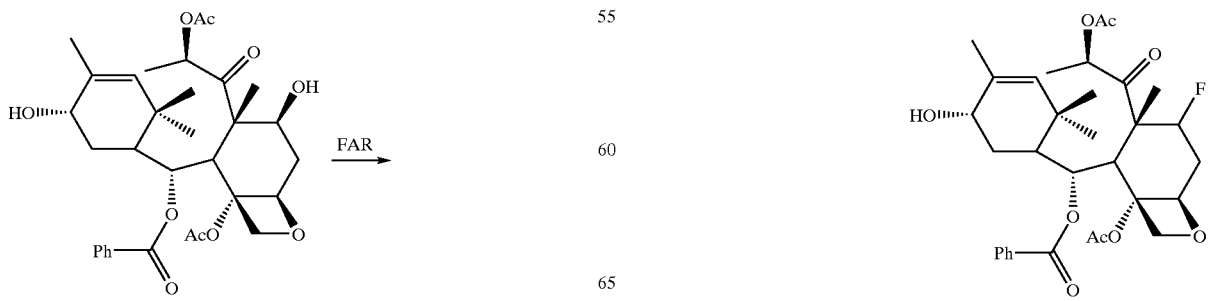

-continued

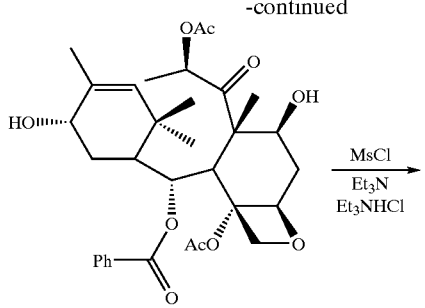

As shown in Reaction Scheme 11, 1-deoxy-baccatin III may be converted into 7-fluoro 1-deoxy-baccatin III by treatment with FAR at room temperature in THF solution. Other 1-deoxy-baccatin derivatives with a free C7 hydroxyl group behave similarly. Alternatively, 7-1-deoxy-chloro baccatin III can be prepared by treatment of baccatin III with methane sulfonyl chloride and triethylamine in methylene chloride solution containing an excess of triethylamine hydrochloride.

Taxanes having C7 acyloxy substituents can be prepared as set forth in Reaction Scheme 12. 7,13-protected 10-oxo-derivative 42 is converted to its corresponding C13 alkoxide by selectively removing the C13 protecting group and replacing it with a metal such as lithium. The alkoxide is then reacted with a β-lactam or other side chain precursor. Subsequent hydrolysis of the C7 protecting groups causes a migration of the C7 hydroxy substituent to C10, migration of the C10 oxo substituent to C9, and migration of the C9 acyloxy substituent to C7.

1-deoxy taxanes having alternative C6 substituents can be prepared using the reactions described in Liang et al., *Tetrahedron Letters*, Vol. 36, No. 17, pp. 2901–2904 (1995), starting, however, with 1-deoxy-10,13-protected-10-DAB instead of taxol. According to this reaction scheme, 1-deoxy-10,13-protected-10-DAB is converted to the 7-0-triflate

REACTION SCHEME 12

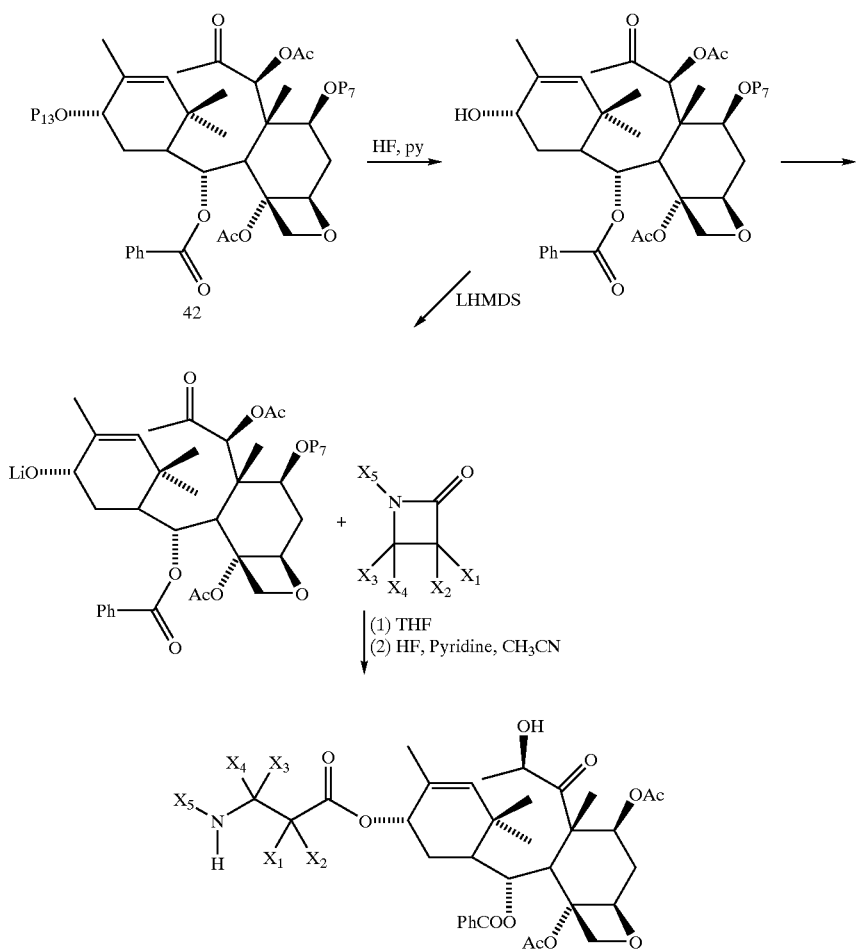

using $CF_3SO_2Cl$. Treatment of the 7-0-triflate with 1,8-diazabicyclo(5,4,0)-undec-7-ene (DBU) produces the 7-deoxy intermediate which when reacted with $OsO_4$ followed by an acid chloride (or chloroformate) yields the corresponding C6 ester or carbonate.

As used herein, "Ar" means aryl; "Ph" means phenyl; "Bz" means benzoyl; "Me" means methyl; "Et" means ethyl; "iPr" means isopropyl; "tBu" and "t-Bu" means tert-butyl; "R" means lower alkyl unless otherwise defined; "Ac" means acetyl; "py" means pyridine; "TES" means triethylsilyl; "TMS" means trimethyl-silyl; "TBS" means $Me_2$t-BuSi-; "Tf" means $—SO_2CF_3$; "BMDA" means $BrMgNiPr_2$; "Swern" means $(COCl)_2$, $Et_3N$; "LTMP" means lithium tetramethylpiperidide; "MOP" means 2-methoxy-2-propyl; "BOM" means benzyloxymethyl; "LDA" means lithium diisopropylamide; "LAH" means lithium aluminum hydride; "Red-Al" means sodium bis(2-methoxyethoxy) aluminum hydride; "Ms" means $CH_3SO_2—$; "TASF" means tris(diethylamino)-sulfonium-difluorotrimethylsilicate; "Ts" means toluene-sulfonyl; "TBAF" means tetrabutyl ammonium hydride; "TPAP" means tetrapropyl-ammonium perruthenate; "DBU" means diazabicycloundecane; "DMAP" means p-dimethylamino pyridine; "LHMDS" means lithium hexamethyldisilazide; "DMF" means dimethylformamide; "AIBN" means azo-(bis)-isobutyronitrile; "10-DAB" means 10-desacetylbaccatin III; "FAR" means 2-chloro-1,1,2-trifluorotriethylamine; "mCPBA" means meta-chloroperbenzoic acid; "DDQ" means dicyanodichloroquinone; "sulfhydryl protecting group" includes, but is not limited to, hemithioacetals such as 1-ethoxyethyl and methoxymethyl, thioesters, or thiocarbonates; "amine protecting group" includes, but is not limited to, carbamates, for example, 2,2,2-trichloroethylcarbamate or tertbutylcarbamate; "protected hydroxy" means —OP wherein P is a hydroxy protecting group; and "hydroxy protecting group" includes, but is not limited to, acetals having two to ten carbons, ketals having two to ten carbons, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-tri-chloroethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, sulfhydryl and amine protecting groups may be found in "Protective Groups in Organic Synthesis" by T. W. Greene, John Wiley and Sons, 1981.

The "hydrocarbon" moities described herein are organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms.

The alkyl groups described herein are preferably lower alkyl containing from one to six carbon atoms in the principal chain and up to 20 carbon atoms. They may be straight or branched chain and include methyl, ethyl, propyl, isopropyl, butyl, hexyl and the like. They may be substituted with aliphatic or cyclic hydrocarbon radicals or hetero-substituted with the various substituents defined herein.

The alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like. They may be substituted with aliphatic or cyclic hydrocarbon radicals or hetero-substituted with the various substituents defined herein.

The alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like. They may be substituted with aliphatic or cyclic hydrocarbon radicals or hetero-substituted with the various substituents defined herein.

The aryl moieties described herein contain from 6 to 20 carbon atoms and include phenyl. They may be hydrocarbon or heterosubstituted with the various substituents defined herein. Phenyl is the more preferred aryl.

The heteroaryl moieties described are heterocyclic compounds or radicals which are analogous to aromatic compounds or radicals and which contain a total of 5 to 20 atoms, usually 5 or 6 ring atoms, and at least one atom other than carbon, such as furyl, thienyl, pyridyl and the like. The heteroaryl moieties may be substituted with hydrocarbon, heterosubstituted hydrocarbon or hetero-atom containing substituents with the hetero-atoms being selected from the group consisting of nitrogen, oxygen, silicon, phosphorous, boron, sulfur, and halogens. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido.

The heterosubstituted hydrocarbon moieties described herein are hydrocarbon moieties which are substituted with at least one atom other than carbon, including moieties in which a carbon chain atom is substituted with a hetero atom such as nitrogen, oxygen, silicon, phosphorous, boron, sulfur, or a halogen atom. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido.

The acyl moieties described herein contain hydrocarbon, substituted hydrocarbon or heteroaryl moieties.

The alkoxycarbonyloxy moieties described herein comprise lower hydrocarbon or substituted hydrocarbon moieties.

The following examples illustrate the invention.

EXAMPLE

Reaction Scheme 1

Hydroxyketone 2. To a stirred solution of 3,10-diol 1 (3.49 g, 14.78 mmol) in 35 mL of DMF under nitrogen at 0° C. was added pyridinium dichromate ("PDC") (7.20 g, 19.15 mmol) as a solid in three portions over a 30 min. period. The reaction mixture was then warmed to room temperature. After 6 h, the reaction mixture was poured into 500 mL of $H_2O$ and extracted with three 200 mL portions of 15% ethyl acetate in hexane. The organic layers were combined and dried over anhydrous $Na_2SO_4$. Removal of the solvent followed by flash chromatography purification (10% EtOAc/hexane) gave 3.34 g (97% yield) of the desired hydroxyketone 2 as a white solid.

2: mp: 73–74° C.; $^1$H NMR (300 MHz, $CDCl_3$) δ (ppm) 0.96 (s, 3H, Me16), 1.06 (s, 3H, Me17), 1.20 (d, J=7.1 Hz, 3H, Me19), 1.38 (d, J=14.8 Hz, 1H, H2α), 1.70 (d, J=1.7 Hz, 3H, Me18), 1.76 (t, J=6.0 Hz, 1H, H1), 2.00 (br d, J=18.1 Hz, 1H, H14α), 2.07 (dd, J=19.2, 7.7 Hz, 1H, H9β), 2.45 (br d, J=18.1 Hz, 1H, H14β), 2.61 (ddq, J=11.5, 7.7, 7.1 Hz, 1H, H8α), 2.66 (dd, J=14.8, 6.0 Hz, 1H, H2β), 2.72 (dd, J=19.2, 11.5 Hz, 1H9α), 2.81 (s, 1H, OH3), 5.43 (m, 1H, H13); $^{13}$C NMR (75 MHz, $CDCl_3$) δ (ppm) 16.40, 21.44, 21.75, 25.46, 33.48, 38.29, 44.68, 44.77, 47.06, 48.41, 73.07, 94.19, 121.72, 138.34, 217.54; IR ($CCl_4$) υ 3520, 3000, 2960, 2900, 2820, 1730, 1440, 1330, 990, 970 cm$^{-1}$; MS (CI) 235 ($M^+$+1, 100) 217 (65).

Triethylsilyl enol ether 3. To a stirred 0.94 M solution of LDA in THF (1.41 mL, 1.33 mmol) under nitrogen at −78° C. was added a solution of hydroxyketone 2 (156 mg, 0.667 mmol) in 1.5 mL of THF and 0.23 mL of HMPA (1.33 mmol) dropwise down the side of the flask. After 0.5 h, a 0.1 M solution (6.67 mL, 0.667 mmol) of TESCl in THF was added down the side of the flask at a rate of 0.1 mL/min. After the addition was complete, the reaction mixture was stirred for an additional 5 min. and then rapidly poured into 50 mL of a vigorously stirred saturated aqueous $NaHCO_3$ solution. The mixture was extracted with three 50 mL portions of hexane and the combined organic layers were washed with 20 mL of $H_2O$, dried over anhydrous $Na_2SO_4$. Removal of the solvent followed by flash chromatography purification (10% EtOAc/hexane) gave 225 mg of triethylsilyl enol ether 3 (97% yield) as a colorless oil.

3: $^1$H NMR (300 MHz, $CDCl_3$) δ (ppm) 0.71 (q, J=7.7 Hz, 6H, TES $CH_2$), 0.89 (s, 3H, Me16), 0.98 (t, J=7.7 Hz, 9H, TES $CH_3$), 1.06 (d, J=7.1 Hz, 3H, Me19), 1.13 (s, 3H, Me17), 1.28 (d, J=14.3 Hz, 1H, H2α), 1.66 (dd, J=6.0, 5.5 Hz, 1H, H1), 1.76 (dd, J=2.2, 1.7 Hz, 3H, Me18), 1.95 (br d, J=18.7 Hz, 1H, H14α), 2.33 (ddd, J=14.3, 6.0, 2.2 Hz, 1H, H2β), 2.42 (br d, J=18.7 Hz, 1H, H14β), 2.72 (qd, J=7.7, 2.1 Hz, 1H, H8α), 3.08 (s, 1H, OH3), 4.45 (d, J=2.1 Hz, 1H, H9), 5.50 (m, 1H, H13); $^{13}$C NMR (75 MHz, $CDCl_3$) δ (ppm) 4.51, 6.46, 16.10, 21.58, 22.76, 25.10, 33.57, 43.78, 44.11, 45.13, 45.16, 71.32, 91.75, 106.27, 120.82, 140.25, 151.77; IR ($CCl_4$) υ 3510, 3010, 2960, 2910, 2880, 2830, 1630, 1440, 1330, 1310, 1230, 1150, 1040, 1010, 880, 700 cm$^{-1}$; MS (CI) 349 ($M^+$+1, 54), 331 (100).

Triethylsilyloxy ketone 4. To a stirred solution of triethylsilyl enol ether 3 (5.335 g, 15.33 mmol) in 300 mL of hexane under nitrogen at 0° C. was added 6.427 g of $NaHCO_3$ (76.55 mmol) and 4.533 g of m-chloroperoxybenzoic acid (67% purity, 17.60 mmol) in four portions over a 0.5 h period. After 2.5 h, the reaction mixture was diluted with 200 mL of hexane and poured into 400 mL of a 1:1 mixture of a saturated aqueous $NaHCO_3$ solution and a saturated aqueous $Na_2S_2O_3$ solution. The organic layer was separated, and the aqueous layer was extracted with two 100 mL portions of hexane. The combined organic layers were washed with 100 mL of $H_2O$, dried over anhydrous $Na_2SO_4$, and concentrated under reduced pressure to give 5.7 g of a yellowish oil. This material was purified by flash chromatography (5% EtOAc/hexane) to give 5.495 g of triethylsilyloxy ketone 4 (98% yield) as a colorless oil.

4: $^1$H NMR (300 MHz, $CDCl_3$) δ (ppm) 0.65 (q, J=7.7 Hz, 6H, TES $CH_2$), 0.90 (s, 3H, Me16), 0.97 (t, J=7.7 Hz, 9H, TES $CH_3$), 1.06 (s, 3H, Me17), 1.11 (d, J=7.7 Hz, 3H, Me19), 1.39 (d, J=14.8 Hz, 1H, H2α), 1.76 (d, J=1.7 Hz, 3H, Me18), 1.76 (dd, J=6.1, 5.5 Hz, 1H, H1), 2.17 (br d, J=18.7 Hz, 1H, H14α), 2.33 (dq, J=9.3, 7.7 Hz, 1H, H8α), 2.46 (br d, J=18.7 Hz, 1H, H14β), 2.64 (ddd, J=14.8, 6.1, 2.2 Hz, 1H, H2β), 2.79 (br s, 1H, OH3), 3.85 (d, J=9.3 Hz, 1H, H9), 5.54 (m, 1H, H13); $^{13}$C NMR (75 MHz, $CDCl_3$) δ (ppm) 4.90, 6.48, 13.98, 21.47, 21.94 26.94, 33.42, 44.33, 44.49, 46.79, 48.59, 70.51, 83.33, 90.04, 121.71, 138.66, 214.42; IR ($CCl_4$) υ 3520, 3000, 2960, 2920, 2880, 2830, 1730, 1450, 1330, 1220, 1160, 1105, 980, 960, 920, 700 cm$^{-1}$; MS (CI) 365 ($M^+$+1, 34), 347 (100), 335 (42), 233 (35).

Triethylsilyloxy diol 5. To a stirred suspension of 0.263 g (6.932 mmol) of lithium aluminum hydride in 30 mL of ethyl ether under nitrogen at 0° C. was added a solution of 2.527 g (6.932 mmol) of triethylsilyloxy ketone 4 in 20 mL of ethyl ether. The reaction mixture was warmed to room temperature. After 2 h at room temperature, the mixture was recooled to 0° C., diluted with 50 mL of ethyl ether, and quenched by dropwise addition of 2.5 mL of $H_2O$. After stirring another 2 h at room temperature, the white suspension was further diluted with 100 mL of ethyl acetate, dried over anhydrous $Na_2SO_4$, and filtered through a 0.5 inch pad of celite. The filtrate was concentrated under reduced pressure to give 2.434 g of triethylsilyloxy diol 5 (96% yield) as a white solid, which was used without any further purification.

5: mp: 62–63° C.; $^1$H NMR (300 MHz, $CDCl_3$) δ (ppm) 0.62 (q, J=7.7 Hz, 6H, TES $CH_2$), 0.97 (t, J=7.7 Hz, 9H, TES $CH_3$), 1.08 (s, 3H, Me16), 1.09 (d, J=7.1 Hz, 3H, Me19), 1.18 (d, J=14.8 Hz, 1H, H2α), 1.20 (s, 3H, Me17), 1.48 (dd, J=6.6, 6.1 Hz, 1H, H1), 1.84 (d, J=1.7 Hz, 3H, Me18), 1.97 (dq, J=8.8, 7.1 Hz, 1H, H8α), 2.17 (br d, J=18.7 Hz, 1H, H14α), 2.43 (br d, J=18.7 Hz, 1H, H14β), 2.47 (ddd, J=14.8, 6.1, 2.2 Hz, 1H, H2β), 2.74 (br s, 1H, OH3), 4.01 (dd, J=8.8, 8.2 Hz, 1H, H9β), 4.28 (d, J=8.2 Hz, 1H, H10), 5.55 (m, 1H, H13); $^{13}$C NMR (75 MHz, $CDCl_3$) δ (ppm) 5.16, 6.60, 12.82, 21.96, 23.63, 27.76, 33.88, 44.16, 44.96, 45.31, 48.27, 63.33, 81.46, 83.37, 122.03, 141.62; IR ($CCl_4$) υ 3640, 3550, 3020, 2970, 2920, 2890, 2850, 1450, 1330, 1240, 1160, 1140, 1120, 1100, 1080, 1040, 1000, 970, 960, 860, 840, 710 cm$^{-1}$; MS (CI) 367 ($M^+$+1, 21), 349 (100), 337 (22), 319 (42).

Triethylsilyloxy keto diol 6. To a vigorously stirred solution of triethylsilyloxy diol 5 (886 mg, 2.42 mmol) in 25 mL of $CH_2Cl_2$ at 0° C. under nitrogen was added 1.08 mL (3.63 mmol) of Ti(Oi-Pr)$_4$ followed by dropwise addition of 1.82 mL (3.63 mmol) of a 2 M solution of t-BuOOH in hexane. After an additional 2 h, 2.5 mL of dimethyl-sulfide was added and the reaction mixture was warmed in a 42° C. bath to reflux for 12 h. The solvent was evaporated under reduced pressure. The residue was dissolved in 200 mL of THF at room temperature and 0.5 mL of $H_2O$ was added dropwise with vigorously stirring. After 2 h, the resulting white suspension was dried over anhydrous $Na_2SO_4$, and then filtered through a 0.5 inch pad of celite, eluting with two 50 mL portions of ethyl acetate. The filtrate was concentrated under reduced pressure to afford a yellow oil. This oil was purified by flash chromatography (10% EtOAc/hexane) to give 866.7 mg of triethylsilyloxy keto diol 6 (94% yield) as a white solid.

6: mp 106–107° C.; $^1$H NMR (300 MHz, $CDCl_3$) δ (ppm) 0.71 (q, J=7.7 Hz, 6H, TES $CH_2$), 1.01 (t, J=7.7 Hz, 9H, TES $CH_3$), 1.01 (s, 3H, Me17), 1.07 (d, J=7.1 Hz, 3H, Me19), 1.53 (s, 3H, Me16), 1.73 (s, 3H, Me18), 1.80–1.94 (m, 3H, H1, H2β, H14α), 2.02 (d, J=3.3 Hz, 1H, OH10), 2.22 (dq, J=9.9, 7.1 Hz, 1H, H8α), 2.52 (d, J=12.1 Hz, 1H, OH13), 2.81 (dd, J=11.5, 3.3 Hz, 1H, H2α) 2.83 (m, 1H, H14β), 4.08 (br t, J=11.5 Hz, 1H, H13), 4.16 (dd, J=9.9, 8.8 Hz, 1H, H9), 4.56 (dd, J=8.8, 3.3 Hz, 1H, H10); $^{13}$C NMR (75 MHz, CDCl$_3$) δ (ppm) 5.36, 6.72, 15.84, 17.96, 26.11, 29.30 34.83, 38.44, 41.00, 45.98, 54.49, 66.94, 77.15, 77.21, 137.66, 140.65, 215.86; IR (CCl$_4$) υ 3650, 3550, 3460, 2980, 2900, 2870, 1670, 1455, 1410, 1370, 1280, 1240, 1210, 1160, 1090, 1050, 1030, 1010, 960, 860, 720 cm$^{-1}$; MS (EI) 382 (M$^+$, 2), 353 (10), 335 (5), 307 (4), 250 (4), 215 (67), 75 (100).

t-Butyldimethylsilyloxy ketone 7. To a stirred solution of triethylsilyloxy keto diol 6 (883 mg, 2.31 mmol) in 35 mL of pyridine under nitrogen at 0° C. was added dropwise 0.485 mL (2.771 mmol) of TBSOTf. The solution was then warmed to room temperature. After 2 h at room temperature, the solution was diluted with 100 mL of hexane and poured into 150 mL of a saturated aqueous NaHCO$_3$ solution. The organic layer was separated, and the aqueous layer was extracted with two 100 mL portions of hexane. The organic layers were combined, and washed with 50 mL of a 10% aqueous CuSO$_4$ solution followed by 20 mL of H$_2$O, and dried over anhydrous Na$_2$SO$_4$. Removal of the solvent followed by flash chromatography purification (2.5% EtOAc/hexane) to give 1.122 g of t-butyldimethylsilyloxy ketone 7 (98% yield) as a white solid.

7: mp: 128–130° C.; $^1$H NMR (300 MHz, CDCl$_3$) δ (ppm) 0.04 (s, 3H, TBS CH$_3$), 0.06 (s, 3H, TBS CH$_3$), 0.63 q, J=7.7 Hz, 6H, TES CH$_2$), 0.93 (s, 9H, TBS t-Bu), 1.01 (t, J=7.7 Hz, 9H, TES CH$_3$), 1.06 (d, J=7.1 Hz, 3H, Me19), 1.09 (s, 3H, Me17), 1.56 (s, 3H, Me16), 1.66 (d, J=1.1 Hz, 3H, Me18), 1.82 (m, 1H, H1), 1.85 (m, 1H, H2β), 1.90 (d, J=3.3 Hz, 1H, OH10), 1.93 (dd, J=14.3, 5.5 Hz, 1H, H14α), 2.16 (dq, J=10.4, 7.1 Hz, 1H, H8α), 2.49 (ddd, J=14.3, 7.8, 2.2 Hz, 1H, H14β), 2.72 (dd, J=12.1, 2.7 Hz, 1H, H2α), 4.19 (dd, J=10.4, 8.8 Hz, 1H, H9), 4.46 (ddd, J=7.8, 5.5, 1.1, 1H, H13), 4.58 (dd, J=8.8, 3.3 Hz, 1H, H10); $^{13}$C NMR (75 MHz, CDCl$_3$) δ (ppm) –5.48, –4.54, 5.33, 6.68, 15.30, 16.42, 17.77, 25.65, 27.15, 27.38, 33.93 38.94, 41.26, 45.83, 53.87, 67.27, 77.23, 77.61, 135.08, 142.06, 209.77; IR (CCl$_4$) υ 3530, 2950, 2930, 2870, 1670, 1460, 1250, 1090, 1030, 1010, 970, 910, 870, 830, 770, 740 cm$^{-1}$; MS (CI) 497 (M$^+$+1, 16), 479 (100), 365 (28), 346 (35), 307 (22), 205 (91).

Trimethylsilyl enol ether 8. To a stirred solution of t-butyldimethylsilyloxy ketone 7 (287 mg, 0.55 mmol) in 2.5 mL of THF and 0.3 mL of HMPA (3.3 mmol) under nitrogen at room temperature, was added dropwise a solution of 0.44 M LDA in THF (3.8 mL, 1.65 mmol). After stirring at room temperature for 10 min., a 1.0 M solution of TMSCl (1.7 mL, 1.65 mmol) in THF was added dropwise at a rate of 0.1 mL/min. After the addition was complete, the reaction was stirred for another 2 minutes. Then 2.5 mL of triethylamine was added and the reaction mixture was poured into 150 mL of a saturated aqueous NaHCO$_3$ solution. The aqueous layer was extracted with three 50 mL portions of hexane. The combined organic layers were washed with 50 mL of H$_2$O, dried over anhydrous Na$_2$SO$_4$ and concentrated under reduced pressure to give 370 mg of trimethylsilyl enol ether 8 (99% yield) as a colorless oil. This material was used in the next step without further purification.

8: $^1$H NMR (500 MHz, CDCl$_3$) δ (ppm) 0.08 (s, 3H, TBS CH$_3$), 0.11 (s, 3H, TBS CH$_3$), 0.14 (s, 9H, TMS CH$_3$), 0.16 (s, 9H, enol TMS CH$_3$), 0.63 (q, J=7.5 Hz, 6H, TES CH$_2$), 0.81 (d, J=7.0 Hz, 3H, Me19), 0.92 (s, 9H, TBS t-Bu), 0.98 (t, J=7.5 Hz, 9H, TES CH$_3$), 1.09 (s, 3H, Me17), 1.23 (ddd, J=14.0, 10.5, 5.5 Hz, 1H, H14α), 1.24 (s, 3H, Me16), 1.81 (d, J=1.5 Hz, 3H, Me18), 1.96 (ddd, J=10.5, 8.5, 5.5 Hz, 1H, H1), 2.30 (dq, J=7.0, 7.0 Hz, 1H, H8α), 2.51 (ddd, J=14.0, 10.5, 7.5 Hz, 1H, H14β), 3.77 (dd, J=7.0, 6.4 Hz, 1H, H9), 4.63 (d, J=6.4 Hz, 1H, H10), 4.67 (ddd, J=10.5, 7.5, 1.5 Hz, 1H, H13), 4.95 (d, J=8.5 Hz, 1H, H2); $^{13}$C NMR (75 MHz, CDCl$_3$) δ (ppm) –5.27, –4.71, 1.06, 0.53, 4.96, 6.86, 12.94, 15.72, 18.11, 25.77, 28.76, 32.02, 37.54, 40.70, 41.79, 41.90, 69.53, 78.61, 80.96, 112.22, 139.48, 139.87, 155.26; IR (CHCl$_3$) υ 2960, 2880, 2870, 1680, 1630, 1460, 1250, 1130, 1080, 1000, 900, 880, 830 cm$^{-1}$; MS (CI) 641 (M$^+$+1, 9), 551 (65), 508 (100), 379 (80).

Hydroxy ketone 9. To a stirred solution of 321 mg (0.501 mmol) of trimethylsilyl enol ether 8 in 15 mL of THF under nitrogen at 0° C. was added 216 mg (80% pure, 1.00 mmol) of m-chloroperoxybenzoic acid as a solid in three portions. After 3 h, the reaction mixture was diluted with 50 mL of hexane and poured into 200 mL of a 1:1 mixture of a saturated aqueous NaHCO$_3$ solution and a saturated aqueous Na$_2$S$_2$O$_3$ solution. The organic layer was separated, and the aqueous layer was extracted with three 100 mL portions of hexane. The combined organic layers were washed with 100 mL of H$_2$O, dried over anhydrous Na$_2$SO$_4$, and concentrated under reduced pressure to give 332 mg of the corresponding trimethyl-silyloxy epoxide as a white solid. This material was used in the next step without further purification.

A solution of 332 mg of the above trimethylsilyloxy epoxide (ca. 0.501 mmol) in 5 mL of methanol and 0.5 mL of CHCl$_3$ was stirred at room temperature for 24 h. Removal of the solvent followed by flash chromatography purification (5% EtOAc/hexane) gave 266 mg of hydroxy ketone 9 as a white solid (91% yield from trimethylsilyl enol ether 8).

9: mp: 111–112° C.; $^1$H NMR (300 MHz, CDCl$_3$) δ (ppm) 0.04 (s, 3H, TBS CH$_3$), 0.07 (s, 3H, TBS CH$_3$), 0.18 (s, 9H, TMS CH$_3$), 0.62 (q, J=7.7 Hz, 6H, TES CH$_2$), 0.93 (s, 9H, TBS t-Bu), 0.97 (t, J=7.7 Hz, 9H, TES CH$_3$), 1.06 (d, J=7.1 Hz, 3H, Me19), 1.08 (s, 3H, Me17), 1.35 (s, 3H, Me16), 1.65 (s, 3H, Me18), 1.81 (dd, J=14.8, 4.4 Hz, 1H, H14α), 1.95 (dd, J=7.7, 3.8 Hz, 1H, H1), 2.26 (ddd, J=14.8, 10.4, 7.7 Hz, 1H, H14β), 2.30 (dq, J=10.4, 7.1 Hz, 1H, H8α), 3.30 (d, J=8.3 Hz, 1H, OH2), 4.22 (dd, J=10.4, 8.8 Hz, 1H, H9), 4.35 (br dd, J=10.4, 4.4 Hz, 1H, H13), 4.41 (dd, J=8.3, 3.8 Hz, 1H, H2), 4.54 (d, J=8.8 Hz, 1H, H10); $^{13}$C NMR (75 MHz, CDCl$_3$) δ (ppm) –5.44, –4.52, 0.95, 4.85, 6.81, 15.46, 17.62, 17.83, 25.65, 26.22, 28.21, 28.39, 36.69, 52.19, 54.33, 66.94, 71.25, 75.74, 77.43, 137.10, 140.25, 211.59; IR (CCl$_4$) υ 3530, 2960, 2890, 2870, 1680, 1460, 1240, 1160, 1120, 1080, 1060, 1020, 1000, 990, 880, 830 cm$^{-1}$; MS (CI) 585 (M$^+$+1, 34), 584 (69), 567 (13), 453 (100), 363 (30), 323 (52).

Triol 10. To a solution of 4-bromo-4-penten-1-ol (770.0 mg, 4.7 mmol) in 20 mL of Et$_2$O at –78° C. under N$_2$ was added a 1.7 M solution of t-BuLi (8 mL, 13.6 mmol) in hexane. The solution was then stirred at 0° C. for 2 h. After cooling to –10° C., a solution of hydroxy ketone 9 (370 mg, 0.63 mmol) in 5 mL of Et$_2$O was added. The solution was stirred at –10° C. for 0.5 h, and then poured into 150 mL of a saturated aqueous NaHCO$_3$ solution. The aqueous layer was extracted with EtOAc (100 mL, 3 times). The combined organic layers were dried over Na$_2$SO$_4$, and the solvent was removed under reduced pressure. The residue was purified by flash chromatography (20% EtOAc/hexane) to give 400 mg (95% yield) of the desired triol 10 as a colorless oil.

10: $^1$H NMR (500 MHz, CDCl$_3$): δ (ppm) 0.136 (s, 12H, TMS CH$_3$, TBS CH$_3$), 0.159 (s, 3H, TBS CH$_3$), 0.669 (qd, J=8.0, 1.5 Hz, 6H, TES CH$_2$), 0.770 (d, J=7.0 Hz, 3H, Me19), 0.921 (s, 9H, TBS t-Bu), 0.991 (t, J=8.0 Hz, 9H, TES CH₃), 1.038 (s, 3H, Me17), 1.488 (s, 3H, Me16), 1.702 (t, J=6.0 Hz, 1H, OH7), 1.729 (s, 3H, Me18), 1.779–1.830 (m, 3H, 2×H6, H8), 1.869 (dd, J=9.0, 2.8 Hz, 1H, H1), 2.101 (m, 2H, 2×H5), 2.134 (d, J=16.0 Hz, 1H, H14α), 2.545 (dt, J=16.0, 9.0 Hz, 1H, H14β), 2.905 (br, 1H, OH2), 3.473 (s, 1H, OH3), 3.670–3.726 (m, 2H, 2×H7), 4.060 (m, 1H, H2β), 4.070 (dd, J=8.0, 6.5 Hz, 1H, H9β), 4.250 (d, J=8.0 Hz, 1H, H10α), 4.322 (d, J=9.0 Hz, 1H, H13β), 4.968 (s, 1H, 1×H20), 5.190 (s, 1H, 1×H20); $^{13}$C NMR (75 MHz, CDCl₃): δ (ppm) −5.19, −4.57, 0.89, 5.05, 6.83, 13.10, 17.74, 19.33, 25.54, 26.18, 28.64, 29.94, 30.97, 34.40, 35.78, 45.27, 51.44, 62.31, 68.88, 73.80, 79.87, 83.83, 109.95, 135.03, 142.32; IR (CHCl₃): υ 2950, 2870, 1090, 1060, 980, 890 cm$^{-1}$; MS (CI): 653 (M$^+$+1−H₂O), 539, 521, 503, 449, 431, 407, 390, 316, 294, 244.

Carbonate 11. To a solution of triol 10 (405 mg, 0.60 mmol) in 20 mL of CH₂Cl₂ at −78° C. under N₂ was added 4.7 mL (60.0 mmol) of pyridine, followed by a solution of COCl₂ (6.0 mL, 6.0 mmol) in toluene. The mixture was then warmed to 0° C. and stirred at that temperature for 50 minutes. Then the mixture was diluted with 100 mL of EtOAc and poured into 200 mL of a saturated aqueous NaHCO₃ solution. The organic layer was separated, and aqueous layer was extracted with EtOAc (100 mL, 3 times). The organic layers were combined and dried over Na₂SO₄. Removal of the solvent gave the desired carbonate 11 a pale yellow oil, which was used without further purification.

11: $^1$H NMR (500 MHz, CDCl₃): δ (ppm) 0.085 (s, 3H, TBS CH₃), 0.100 (s, 12H, TBS CH₃, TMS CH₃), 0.652 (qd, J=7.5, 1.5 Hz, 6H, TES CH₂), 0.912 (s, 9H, TBS t-Bu), 0.950 (d, J=6.0 Hz, 3H, Me19), 0.984 (t, J=7.5 Hz, 9H, TES CH₃), 1.199 (s, 3H, Me17), 1.434 (ddd, J=18.5, 9.0, 4.5 Hz, 1H, H14α), 1.481 (s, 3H, Me16), 1.637 (m, 1H, 1×H6), 1.722 (m, 1H, 1×H6), 1.786 (d, J=1.0 Hz, 3H, Me18), 2.192–2.349 (m, 4H, 2×H5, H1, H14β), 2.396 (qd, J=6.0, 5.0 Hz, 1H, H8), 3.658 (qd, J=6.5, 3.0 Hz, 2H, 2×H7), 3.982 (dd, J=8.0, 5.0 Hz, 1H, H9β), 4.509 (d, J=8.0 Hz, 1H, H10α), 4.771 (td, J=9.0, 1.0 Hz, 1H, H13β), 4.858 (d, J=4.0 Hz, 1H, H2), 5.275 (s, 2H, 2×H20).

Acetate 12. To a solution of the above carbonate 11 in 5 mL of pyridine at room temperature under N₂ was added Ac₂O (0.6 mL, 6.3 mmol). After stirring at room temperature for 9 h, the solution was diluted with 100 mL of 20% EtOAc in hexane, and poured into 100 mL of a saturated aqueous NaHCO₃ solution. The organic layer was separated, and the aqueous layer was extracted with 20% EtOAc in hexane (100 mL, 3 times). The organic layers were combined and dried over Na₂SO₄. Removal of the solvent followed by flash chromatography purification (8% EtOAc/hexane) gave 433.2 mg (98% yield) of the desired acetate 12 as a colorless oil.

12: $^1$H NMR (500 MHz, CDCl₃): δ (ppm) 0.085 (s, 3H, TBS CH₃), 0.097 (s, 12H, TMS CH₃, TBS CH₃), 0.654 (qd, J=8.0, 2.0 Hz, 6H, TES CH₂), 0.913 (s, 9H, TBS t-Bu), 0.935 (d, J=7.5 Hz, 3H, Me19), 0.985 (t, J=8.0 Hz, 9H, TES CH₃), 1.201 (s, 3H, Me17), 1.429 (m, 1H, H14α), 1.480 (s, 3H, Me16), 1.711 (m, 1H, 1×H6), 1.788 (s, 3H, Me18), 1.820 (m, 1H, 1×H6), 2.041 (s, 3H, COCH₃), 2.153–2.351 (m, 4H, H1, 2×H5, H14β), 2.403 (dq, J=8.0, 7.5 Hz, 1H, H8), 3.977 (dd, J=8.0, 5.5 Hz, 1H, H9β), 4.075 (t, J=6.5 Hz, 2H, 2×H7), 4.510 (d, J=8.0 Hz, 1H, H10α), 4.771 (t, J=8.0 Hz, 1H, H13β), 4.835 (d, J=4.0 Hz, 1H, H2β), 5.253 (s, 1H, 1×H20), 5.286 (s, 1H, 1×H20); $^{13}$C NMR (75 MHz, CDCl₃): δ (ppm) −5.37, −4.74, 0.79, 4.98, 6.74, 12.93, 15.61, 17.92, 20.53, 25.63, 27.36, 28.27, 29.77, 32.34, 32.98, 36.48, 39.11, 48.96, 63.55, 68.84, 73.02, 79.66, 88.61, 92.86, 114.68, 137.48, 141.39, 150.56, 154.08, 171.14; IR (CHCl₃): υ 2950, 2850, 1790, 1713, 1020, 880, 815 cm$^{-1}$; MS (CI): 739 (M$^+$+1), 691, 665, 607, 563, 503, 473, 431.

Hydroxy alkene 13. To a solution of acetate 12 (433.0 mg, 0.586 mmol) in 2 mL of CH₃CN at 0° C. was added 5.0 mL of a solution of 48% HF/pyridine/CH₃CN (1:8:8). After stirring at 0° C. for 3 h, the solution was diluted with 50 mL of EtOAc and poured into 100 mL of a saturated aqueous NaHCO₃ solution. The organic layer was separated, and the aqueous layer was extracted with EtOAc (100 mL, 3 times). The organic layers were combined and dried over Na₂SO₄. Removal of the solvent gave a pale yellow oil, which was used without further purification To a solution of the above oil in 4 mL of CH₂Cl₂ at room temperature under N₂ was added Et₃N (0.32 mL, 2.3 mmol), followed by TESCl (0.20 mL, 1.2 mmol). After stirring at room temperature for 1.5 h, the solution was diluted with 100 mL of 20% EtOAc in hexane, and poured into 100 mL of a saturated aqueous NaHCO₃ solution. The organic layer was separated, and the aqueous layer was extracted with 20% EtOAc in hexane (100 mL, 3 times). The organic layers were combined and dried over Na₂SO₄. Removal of the solvent followed by flash chromatography purification (15% EtOAc/hexane) gave 351.0 mg of the desired hydroxy alkene 13 (90% yield) as a colorless oil, plus 2.3% starting material 12 and 1.1% 9,10-diol.

13: $^1$H NMR (500 MHz, CDCl₃): δ (ppm) 0.090 (s, 3H, TBS CH₃), 0.104 (s, 3H, TBS CH₃), 0.662 (qd, J=8.0, 1.5 Hz, 6H, TES CH₂), 0.915 (s, 9H, TBS t-Bu), 0.965 (d, J=7.5 Hz, 3H, Me19), 0.989 (t, J=8.0 Hz, 9H, TES CH₃), 1.197 (s, 3H, Me17), 1.486 (s, 3H, Me16), 1.434 (dd, J=9.5, 4.7 Hz, 1H, H14α), 1.780 (m, 1H, 1×H6), 1.810 (d, J=1.5 Hz, 3H, Me18), 1.942 (m, 1H, 1×H6), 2.045 (s, 3H, COCH₃), 2.191 (m, 1H, 1×H5), 2.208 (d, J=2.5 Hz, 1H, OH9), 2.262–2.333 (m, 3H, 1×H5, H1, H8), 2.360 (m, 1H, H14β), 3.986 (m, 1H, H9β), 4.112 (td, J=6.5, 2.5 Hz, 2H, 2×H7), 4.512 (d, J=8.5 Hz, 1H, H10α), 4.760–4.791 (m, 2H, H13β, H2), 5.201 (s, 1H, 1×H20), 5.320 (s, 1H, 1×H20); $^{13}$C NMR (75 MHz, CDCl₃): δ (ppm) −5.41, −4.72, 4.64, 5.49, 11.23, 15.89, 17.88, 20.52, 25.60, 27.13, 27.44, 28.09, 32.49, 33.16, 36.72, 36.83, 49.11, 63.52, 68.78, 70.99, 79.13, 86.15, 92.71, 114.00, 136.37, 141.98, 147.57, 154.21, 171.20; IR (CHCl₃): υ 2960, 2780, 1795, 1735, 1000, 865 cm$^{-1}$; MS (CI): 667 (M$^+$+1), 649, 623, 605, 587, 535, 473.

Ketone 14. To a mixture of hydroxy alkene 13 (343.0 mg, 0.515 mmol) and 200 mg of 3A° molecular sieves in 5 mL of CH₂Cl₂ at room temperature under N₂ was added 4-methyl-morpholine (180 mg, 1.54 mmol) followed by tetra-propylammonium perruthenate (18 mg, 0.05 mmol). After stirring at room temperature for 2 h, the mixture was filtered through a short pad of silica gel. The silica gel was washed with 200 mL of 15% EtOAc in hexane. Removal of the solvent gave 338.5 mg of the desired ketone 14 (99% yield) as a colorless oil, which was used without any further purification.

14: $^1$H NMR (500 MHz, CDCl₃): δ (ppm) 0.116 (s, 3H, TBS CH₃), 0.132 (s, 3H, TBS CH₃), 0.635 (qd, J=7.5, 4.0 Hz, 6H, TES CH₂), 0.936 (s, 9H, TBS t-Bu), 0.961 (t, J=7.5 Hz, 9H, TES CH₃), 1.051 (d, J=7.0 Hz, 3H, Me19), 1.203 (s, 3H, Me17), 1.232 (s, 3H, Me16), 1.534 (m, 1H, H14α), 1.807 (m, 1H, 1×H6), 1.885–1.981 (m, 2H, 1×H5, 1×H6), 1.942 (d, J=1.5 Hz, 3H, Me18), 2.059 (s, 3H, COCH₃), 2.242 (ddd, J=15.5, 10.5, 4.0 Hz, 1H, 1×H5), 2.333–2.418 (m, 2H, H14β, H1), 3.523 (q, J=7.0 Hz, 1H, H8), 4.103 (t, J=6.0 Hz, 2H, 2×H7), 4.773 (d, J=4.5 Hz, 1H, H2β), 4.868 (m, 1H, H13β), 4.935 (s, 1H, H10α), 5.282 (s, 1H, 1×H20), 5.320 (s, 1H, 1×H20); $^{13}$C NMR (75 MHz, CDCl₃): δ (ppm)

−5.44, −4.78, 4.60, 6.34, 15.11, 15.54, 17.91, 20.53, 25.60, 25.68, 27.01, 28.00, 32.35, 32.88, 36.69, 42.40, 47.82, 63.46, 68.70, 79.56, 85.00, 90.58, 115.91, 134.62, 143.46, 145.91, 153.47, 171.15, 209.74; IR (CHCl$_3$): υ 2960, 2880, 1800, 1750, 1000, 865 cm$^{-1}$; MS (CI): 665 (M$^+$+1), 648, 637, 621, 533, 489.

Hydroxy ketone 15. To a 0.1 M solution of Pd(acac)$_2$/n-Bu$_3$P (1:1) in DMF (1 mL, 0.1 mmol) at room temperature under N$_2$ was added a 2.37 M solution of HCOOH/Et$_3$N (1:1) in DMF (10.2 mL, 24.2 mmol), followed by a solution of ketone 14 (320.0 mg, 0.48 mmol) in 5 mL of DMF. After stirring at room temperature for 19 h, the solution was diluted with 100 mL of Et$_2$O and poured into 100 mL of a saturated aqueous NaHCO$_3$ solution. The organic layer was separated, and the aqueous layer was extracted with Et$_2$O (100 mL, 3 times). The organic layers were combined and dried over Na$_2$SO$_4$. Removal of the solvent followed by flash chromatography purification (15% EtOAc/hexane) gave 280.5 mg (94% yield) of the desired hydroxy ketone 15 as a colorless oil.

15: $^1$H NMR (500 MHz, CDCl$_3$): δ (ppm) 0.138 (s, 3H, TBS CH$_3$), 0.149 (s, 3H, TBS CH$_3$), 0.628 (qd, J=7.5, 3.0 Hz, 6H, TES CH$_2$), 0.892 (d, J=7.0 Hz, 3H, Me19), 0.953 (s, 9H, TBS t-Bu), 0.962 (t, J=7.5 Hz, 9H, TES CH$_3$), 1.104 (s, 3H, Me17), 1.201 (s, 3H, Me16), 1.409 (ddd, J=14.5, 4.5, 4.0 Hz, 1H, H14α), 1.464 (q, J=6.0 Hz, 1H, 1×H5), 1.783 (br, 1H, OH2), 1.805–1.863 (m, 2H, 2×H6), 1.910 (d, J=1.0 Hz, 3H, Me18), 2.054 (m, 1H, H1), 2.063 (s, 3H, COCH$_3$), 2.367–2.473 (m, 3H, H14β, 1×H5, H3), 3.024 (dq, J=9.0, 7.0 Hz, 1H, H8), 3.880 (ddd, J=9.5, 2.5, 2.0 Hz, 1H, H2β), 4.102 (m, 1H, 1×H7), 4.154 (m, 1H, 1×H7), 4.790 (ddd, J=9.0, 4.5, 1.0 Hz, 1H, H13β), 4.899 (s, 1H, H10α), 5.012 (s, 1H, 1×H20), 5.097 (s, 1H, 1×H20).

Hydroxy ketone 16. To a solution of hydroxy ketone 15 (450.0 mg, 0.72 mmol) in 15 mL of CH$_2$Cl$_2$ at room temperature under N$_2$ was added diisopropylethylamine (1.25 mL, 7.2 mmol), followed by tetrabutylammonium iodide (265.0 mg, 0.72 mmol) and benzyloxymethylchloride (0.5 mL, 3.6 mmol). After stirring at room temperature for 24 h, another 1.25 mL (7.2 mmol) of diisopropylethylamine followed by 0.5 mL (3.6 mmol) of benzyloxymethylchloride was added. The solution was stirred at room temperature for another 24 h, and then was heated to 40° C. for 2 h. After being recooled to room temperature, the solution was diluted with 50 mL of THF and 5 mL of MeOH. Then a 0.1 N aqueous solution of NaOH (10 mL, 1.0 mmol) was added. After stirring at room temperature for 1.5 h, the solution was diluted with 100 mL of 20% EtOAc in hexane, and poured into 50 mL of a saturated aqueous NaHCO$_3$ solution. The organic layer was separated, and the aqueous layer was extracted with 20% EtOAc in hexane (50 mL, 3 times). The organic layers were combined, washed with 50 mL of a saturated aqueous NH$_4$Cl solution, 50 mL of a saturated aqueous NaHCO$_3$ solution, and then dried over Na$_2$SO$_4$. Removal of the solvent followed by flash chromatography purification (20% EtOAc/hexane) gave 430.0 mg (85% yield) of the desired hydroxy ketone 16 as a colorless oil.

16: $^1$H NMR (500 MHz, CDCl$_3$): δ (ppm) 0.140 (s, 3H, TBS CH$_3$), 0.150 (s, 3H, TBS CH$_3$), 0.636 (qd, J=8.0, 4.0 Hz, 6H, TES CH$_2$), 0.939 (d, J=7.0 Hz, 3H, Me19), 0.949 (t, J=8.0 Hz, 9H, TES CH$_3$), 0.967 (s, 9H, TBS t-Bu), 1.078 (s, 3H, Me17), 1.202 (s, 3H, Me16), 1.450 (ddd, J=15.0, 8.5, 5.0 Hz, 1H, H14α), 1.661 (t, J=6.0 Hz, 1H, OH20), 1.695–1.821 (m, 2H, 2×H6), 1.910 (d, J=1.0 Hz, 3H, Me18), 2.055 (m, 1H, 1×H5), 2.174 (m, 1H, H1), 2.258 (m, 1H, 1×H5), 2.317 (m, 1H, H14β), 2.473 (dd, J=10.0, 7.0 Hz, 1H, H3), 3.100 (dq, J=7.0, 7.0 Hz, 1H, H8α), 3.615–3.693 (m, 2H, 2×H7), 3.967 (dd, J=10.0, 3.0 Hz, 1H, H2β), 4.548 (d, J=12.0 Hz, 1H, 1H×BOM), 4.596 (d, J=12.0 Hz, 1H, 1H×BOM), 4.601 (d, J=7.0 Hz, 1H, 1H×BOM), 4.710 (d, J=7.0 Hz, 1H, 1H×BOM), 4.836 (br td, J=8.5, 1.0 Hz, 1H, H13β), 4.868 (s, 1H, H10α), 5.009 (br s, 1H, 1×H20), 5.014 (br s, 1H, 1×H20), 7.277–7.346 (m, 5H, 5H×BOM); $^{13}$C NMR (75 MHz, CDCl$_3$): δ (ppm) −5.34, −4.69, 4.61, 6.48, 15.57, 17.88, 18.03, 25.74, 26.01, 30.05, 32.40, 32.73, 36.60, 37.27, 47.32, 53.74, 62.22, 69.32, 69.69, 79.84, 82.51, 94.65, 113.60, 127.57, 127.70, 128.52, 135.67, 138.25, 141.04, 148.02, 215.16.

Keto aldehyde 17. To a mixture of hydroxy ketone 16 (130.0 mg, 0.186 mmol) and 150 mg of 3A° molecular sieves in 5 mL of CH$_2$Cl$_2$ at room temperature under N$_2$ was added 4-methyl-morpholine (65.0 mg, 0.55 mmol) followed by tetrapropylammonium perruthenate (7.0 mg, 0.02 mmol). After stirring at room temperature for 2 min., the mixture was filtered through a short pad of silica gel. The silica gel was washed with 50 mL of 10% EtOAc in hexane. Removal of the solvent gave 116.8 mg (90% yield) of desired keto aldehyde 17 as a colorless oil, which was used without further purification.

17. $^1$H NMR (300 MHz, CDCl$_3$): δ (ppm) 0.128 (s, 3H, TBS CH$_3$), 0.139 (s, 3H, TBS CH$_3$), 0.615 (qd, J=8.1, 2.1 Hz, 6H, TES CH$_2$), 0.919 (d, J=6.6 Hz, 3H, Me19), 0.948 (t, J=8.1 Hz, 9H, TES CH$_3$), 0.952 (s, 9H, TBS t-Bu), 1.058 (s, 3H, Me17), 1.197 (s, 3H, Me16), 1.413 (m, 1H, H14α), 1.900 (br s, 3H, Me18), 2.159 (m, 1H), 2.239–2.387 (m, 2H), 2.422–2.700 (m, 4H), 3.094 (qd, J=6.6, 6.6 Hz, 1H, H8), 3.954 (dd, J=9.6, 2.7 Hz, 1H, H2), 4.513 (d, J=12.0 Hz, 1H, 1H×BOM), 4.574 (d, J=7.2 Hz, 1H, 1H×BOM), 4.595 (d, J=12.0 Hz, 1H, 1H×BOM), 4.704 (d, J=7.2 Hz, 1H, 1H×BOM), 4.821 (br t, J=8.4 Hz, 1H, H13), 4.848 (s, 1H, H10), 4.905 (br s, 1H, 1×H20), 5.029 (br s, 1H, 1×H20), 7.278–7.360 (m, 5H×BOM), 9.724 (t, J=1.5 Hz, 1H, CHO).

Alkene 18. A 0.08 M solution of BaO in MeOH (10.0 mL) was added to keto aldehyde 17 (116.8 mg, 0.167 mmol) at room temperature under N$_2$. After stirring at room temperature for 9 h, the solution was concentrated under reduced pressure. Then 30 mL of EtOAc and 20 mL of a saturated aqueous NaHCO$_3$ solution were added. The organic layer was separated, and the aqueous layer was extracted with EtOAc (30 mL, 5 times). The organic layers were combined and dried over Na$_2$SO$_4$. Removal of the solvent gave 110.0 mg (94% yield) of the crude product as a pale yellow oil, which was used without further purification.

To a solution of the above crude product (110.0 mg, 0.158 mmol) in 2 mL of pyridine at 0° C. under N$_2$ was added TESOTf (0.11 mL, 0.47 mmol). After stirring at 0° C. for 1 h, the solution was diluted with 30 mL of 10% EtOAc in hexane, and poured into 30 mL of a saturated aqueous NaHCO$_3$ solution. The organic layer was separated, and the aqueous layer was extracted with 10% EtOAc in hexane (30 mL, 3 times). The organic layers were combined and dried over Na$_2$SO$_4$. Removal of the solvent followed by flash chromatography purification (2% EtOAc/hexane) gave 100.0 mg (78% overall yield from hydroxy ketone 16) of the desired alkene 18 as a colorless oil.

18: $^1$H NMR (500 MHz, CDCl$_3$): δ (ppm) 0.099 (s, 3H, TBS CH$_3$), 0.131 (s, 3H, TBS CH$_3$), 0.565 (q, J=8.0 Hz, 6H, TES CH$_2$), 0.635 (qd, J=8.0, 2.5 Hz, 6H, TES CH$_2$), 0.925 (s, 9H, TBS t-Bu), 0.943 (t, J=8.0 Hz, 9H, TES CH$_3$), 0.960 (s, 3H, Me17), 0.995 (t, J=8.0 Hz, 9H, TES CH$_3$), 1.136 (s, 3H, Me19), 1.155 (s, 3H, Me16), 1.561 (m, 1H, H6β), 1.637 (dd, J=15.0, 5.5 Hz, 1H, H14α), 1.794 (br d, J=9.0 Hz, 1H, H1), 1.915 (m, 1H, H6α), 2.043 (d, J=1.5 Hz, 3H, Me18), 2.106–2.162 (m, 2H, 2×H5), 2.500 (dt, J=15.0, 9.0 Hz, 1H, H14β), 3.244 (br d, J=4.0 Hz, 1H, H3), 3.785 (br dd, J=4.0, 1.0 Hz, 1H, H2β), 4.173 (dd, J=11.0, 4.5 Hz, 1H, H7α), 4.565 (m, 1H, H13β), 4.579 (s, 2H, 2H×BOM), 4.680 (d, J=7.0 Hz, 1H, 1H×BOM), 4.703 (d, J=7.0 Hz, 1H, 1H×BOM), 4.929 (br s, 1H, 1×H20), 5.363 (s, 1H, H10α), 5.489 (t, J=2.0 Hz, 1H, 1×H20), 7.270–7.343 (m, 5H, 5H×BOM); $^{13}$C NMR (75 MHz, CDCl$_3$): δ (ppm) −5.33, −4.54, 4.89, 5.92, 6.62, 6.71, 11.53, 17.27, 17.78, 24.95, 25.65, 31.09, 32.40, 32.79, 37.63, 37.83, 47.44, 49.34, 62.19, 68.53, 70.05, 75.00, 76.36, 78.90, 93.74, 113.68, 127.73, 127.90, 128.54, 136.72, 137.17, 138.11, 143.93, 209.62.

Allylic alcohol 19. To a solution of alkene 18 (80.0 mg, 0.0985 mmol) in 5 mL of CH$_2$Cl$_2$ at room temperature under N$_2$ was added 1.0 mL of t-BuOOH (90% pure, 9.8 mmol), followed by SeO$_2$ (109.0 mg, 0.985 mmol). After stirring at room temperature for 10 h, the solution was diluted with 50 mL of 20% EtOAc in hexane and poured into 20 mL of a saturated aqueous NaHCO$_3$ solution. The organic layer was separated and the aqueous layer was extracted with 20% EtOAc in hexane (20 mL, 3 times). The organic layers were combined and washed with 10 mL of water, and then dried over Na$_2$SO$_4$. Removal of the solvent followed by flash chromatography purification (3% EtOAc/hexane) gave 75.0 mg (92% yield) of the desired allylic alcohol 19 as a colorless oil.

19: $^1$H NMR (500 MHz, CDCl$_3$): δ (ppm) 0.135 (s, 3H, TBS CH$_3$), 0.162 (s, 3H, TBS CH$_3$), 0.571 (q, J=8.0 Hz, 6H, TES CH$_2$), 0.640 (qd, J=8.0, 1.5 Hz, 6H, TES CH$_2$), 0.927 (s, 3H, Me17), 0.943 (s, 9H, TBS t-Bu), 0.959 (t, J=8.0 Hz, 9H, TES CH$_3$), 0.995 (t, J=8.0 Hz, 9H, TES CH$_3$), 1.109 (s, 3H, Me19), 1.163 (s, 3H, Me16), 1.564–1.632 (m, 2H, H6β, H14α), 1.792 (br d, J=8.5 Hz, 1H, H1), 2.108 (br, 1H, OH5), 2.123 (d, J=1.0 Hz, 3H, Me18), 2.155 (m, 1H, H6α), 2.550 (dt, J=15.0, 8.5 Hz, 1H, H14β), 3.785 (br d, J=2.0 Hz, 1H, H2β), 3.931 (br t, J=2.0 Hz, 1H, H3), 4.180 (t, J=3.0 Hz, 1H, H5β), 4.570 (s, 2H, 2H×BOM), 4.597 (dd, J=11.5, 4.5 Hz, 1H, H7α), 4.613 (br t, J=8.5 Hz, 1H, H13β), 4.675 (d, J=7.0 Hz, 1H, 1H×BOM), 4.697 (d, J=7.0 Hz, 1H, 1H×BOM), 5.166 (t, J=2.0 Hz, 1H, 1×H20), 5.414 (s, 1H, H10α), 5.742 (t, J=2.0 Hz, 1H, 1×H20), 7.268–7.347 (m, 5H, 5H×BOM).

Diol mesylate 20. To a solution of allylic alcohol 19 (14.0 mg, 0.017 mmol) in 0.7 mL of pyridine at 0° C. under N$_2$ was added MsCl (0.05 mL, 0.645 mmol). The solution was stirred at 0° C. for 2 h. Then 1.5 mL of Et$_2$O followed by 0.22 mL (0.034 mmol) of a 0.157 M solution of OsO$_4$ in THF was added. The mixture was kept at −20° C. for 12 h, and then was diluted with 5 mL of THF. Next, 30 mg of NaHSO$_3$ followed by 0.5 mL of H$_2$O was added. After stirring at room temperature for 8 h, the solution was diluted with 50 mL of EtOAc, and poured into 50 mL of a saturated aqueous NaHCO$_3$ solution. The organic layer was separated, and the aqueous layer was extracted with EtOAc (20 mL, 3 times). The organic layers were combined and dried over Na$_2$SO$_4$. Removal of the solvent gave 15 mg of desired diol mesylate 20 as a pale yellow oil, which was used without further purification.

20: $^1$H NMR (500 MHz, CDCl$_3$): δ (ppm) 0.122 (s, 3H, TBS CH$_3$), 0.173 (s, 3H, TBS CH$_3$), 0.558 (q, J=8.0 Hz, 6H, TES CH$_2$), 0.640 (qd, J=8.0, 5.0 Hz, 6H, TES CH$_2$), 0.949 (t, J=8.0 Hz, 9H, TES CH$_3$), 0.964 (s, 9H, TBS t-Bu), 0.978 (t, J=8.0 Hz, 9H, TES CH$_3$), 1.070 (s, 3H, Me16), 1.085 (s, 3H, Me17), 1.174 (s, 3H, Me19), 1.935 (m, 1H, H6β), 1.977–2.037 (m, 2H, H14α, H1), 2.123 (d, J=1.0 Hz, 3H, Me18), 2.244 (dt, J=15.0, 4.5 Hz, 1H, H6α), 2.316 (dt, J=14.0, 9.0 Hz, 1H, H14β), 2.381 (dd, J=10.5, 1.5 Hz, 1H, OH20), 3.147 (s, 3H, SO$_2$CH$_3$), 3.575 (d, J=6.5 Hz, 1H, H3), 3.607 (t, J=10.5 Hz, 1H, 1×H20), 3.940 (dd, J=10.5, 1.5 Hz, 1H, 1×H20), 3.990 (dd, J=6.5, 2.5 Hz, 1H, H2β), 4.133 (s, 1H, OH4), 4.228 (dd, J=11.5, 4.5 Hz, 1H, H7α), 4.613 (s, 2H, 2H×BOM), 4.766 (d, J=7.0 Hz, 1H, 1H×BOM), 4.825 (m, 1H, H13β), 4.839 (d, J=7.0 Hz, 1H, 1H×BOM), 4.895 (m, 1H, H5β), 5.276 (s, 1H, H10α), 7.298–7.357 (m, 5H, 5B×BOM).

Oxetane 21. To a solution of the above diol mesylate 20 in 1.0 mL of toluene at room temperature under N$_2$ was added DBU (0.06 mL, 0.04 mmol). The solution was then heated to 120° C. (oil bath temperature) for 15 minutes, and kept at 120° C. for another 15 minutes. Removal of the solvent followed by flash chromatography purification (15% EtOAc/hexane) gave 12.5 mg of desired oxetane 21 (87% overall yield from allylic alcohol 19) as a colorless oil.

21: $^1$H NMR (500 MHz, CDCl$_3$): δ (ppm) 0.143 (s, 3H, TBS CH$_3$), 0.154 (s, 3H, TBS CH$_3$), 0.580 (q, J=8.0 Hz, 6H, TES CH$_2$), 0.635 (qd, J=8.0, 2.5 Hz, 6H, TES CH$_2$), 0.952 (t, J=8.0 Hz, 9H, TES CH$_3$), 0.971 (s, 9H, TBS t-Bu), 0.977 (s, 3H, Me17), 0.992 (t, J=8.0 Hz, 9H, TES CH$_3$), 1.116 (s, 3H, Me16), 1.532 (s, 3H, Me19), 1.944 (m, 1H, H1), 1.945 (d, J=1.5 Hz, 3H, Me18), 2.000 (m, 1H, H14α), 2.030 (m, 1H, H6β), 2.407 (dt, J=15.5, 9.5 Hz, 1H, H14β), 2.465 (m, 1H, H6α), 2.990 (s, 1H, OH4), 3.050 (d, J=5.5 Hz, 1H, H3), 3.888 (dd, J=5.5, 2.5 Hz, 1H, H2β), 4.042 (dd, J=11.5, 6.5 Hz, 1H, H7α), 4.358 (d, J=8.0 Hz, 1H, H20α), 4.513 (d, J=12.0 Hz, 1H, 1H×BOM), 4.555 (ddd, J=9.5, 4.5, 1.5 Hz, 1H, H13β), 4.608 (d, J=12.0 Hz, 1H, 1H×BOM), 4.640 (d, J=8.0 Hz, 1H, H20β), 4.645 (d, J=6.5 Hz, 1H, 1H×BOM), 4.713 (d, J=6.5 Hz, 1H, 1H×BOM), 4.730 (dd, J=10.0, 4.0 Hz, 1H, H5α), 5.153 (s, 1H, H10α), 7.270–7.355 (m, 5H, 5H×BOM); $^{13}$C NMR (75 MHz, CDCl$_3$): δ (ppm) −5.21, −4.39, 4.99, 5.77, 6.60, 6.68, 10.32, 16.28, 17.98, 24.45, 25.84, 30.73, 31.31, 37.53, 37.68, 45.36, 50.59, 58.88, 68.15, 70.28, 73.33, 74.74, 76.30, 78.73, 81.39, 86.61, 94.82, 127.69, 128.01, 128.69, 136.43, 137.67, 137.83, 207.89.

Diol 22. To a solution of oxetane 21 (60.0 mg, 0.071 mmol) in 0.1 mL of CH$_3$CN at room temperature was added 1.0 mL of a 48% HF/pyridine/CH$_3$CN (1:3.5:3.5) solution. After stirring at room temperature for 24 h, the solution was diluted with 50 mL of EtOAc, and poured into 20 mL of a saturated aqueous NaHCO$_3$ solution. The organic layer was separated, and the aqueous layer was extracted with EtOAc (20 mL, 3 times). The organic layers were combined and dried over Na$_2$SO$_4$. Removal of the solvent then gave the tetraol as a pale yellow oil, which was used without any further purification.

To a solution of the above oil in 1 mL of pyridine at room temperature was added TESCl (0.06 mL, 0.355 mmol). After stirring at room temperature for 21 h, the solution was diluted with 10 mL of EtOAc, and poured into 20 mL of a saturated aqueous NaHCO$_3$ solution. The organic layer was separated, and the aqueous layer was extracted with EtOAc (20 mL, 3 times). The organic layers were combined and dried over Na$_2$SO$_4$. Removal of the solvent followed by chromatography purification (5% EtOAc/hexane) gave the desired diol 22 (48.0 mg, 93% overall yield) as a colorless oil.

22: $^1$H NMR (500 MHz, CDCl$_3$): δ (ppm) 0.538 (qd, J=8.0, 1.0 Hz, 6H, TES CH$_2$), 0.707 (q, J=8.0 Hz, 6H, TES CH$_2$), 0.919 (t, J=8.0 Hz, 9H, TES CH$_3$), 1.001 (s, 3H, Me17), 1.011 (s, 3H, Me16), 1.026 (t, J=8.0 Hz, 9H, TES CH$_3$), 1.605 (s, 3H, Me19), 1.964–2.037 (m, 3H, H1, H14α, H6β), 2.019 (d, J=1.5 Hz, 3H, Me18), 2.392 (m, 1H, H6α), 2.452 (m, 1H, H14β), 3.090 (d, J=6.0 Hz, 1H, H3), 3.150 (s, 1H, OH4), 3.873 (dd, J=6.0, 3.0 Hz, 1H, H2), 3.988 (dd, J=11.5, 7.5 Hz, 1H, H7α), 4.140 (d, J=3.0 Hz, 1H, OH10), 4.396 (d, J=7.5 Hz, 1H, H20α), 4.527 (d, J=11.5 Hz, 1H, 1H×BOM), 4.599 (br m, 1H, H13β), 4.621 (d, J=11.5 Hz, 1H, 1H×BOM), 4.626 (d, J=7.5 Hz, 1H, H20β), 4.656 (d, J=6.5 Hz, 1H, 1H×BOM), 4.729 (d, J=6.5 Hz, 1H, 1H×BOM), 4.787 (dd, J=9.5, 4.0 Hz, 1H, H5α), 5.106 (d, J=3.0 Hz, 1H, H10), 7.284–7.363 (m, 5H, 5H×BOM); $^{13}$C NMR (75 MHz, CDCl$_3$): δ (ppm) 4.672, 4.945, 6.433, 6.645, 9.878, 16.509, 23.976, 29.500, 30.775, 31.791, 37.406, 45.222, 50.655, 58.288, 68.259, 70.292, 73.494, 74.754, 75.133, 78.639, 81.158, 86.804, 94.907, 127.687, 128.067, 128.704, 136.337, 137.597, 140.025, 212.474.

Bis-acetate 23. To a solution of diol 22 (5.0 mg, 0.007 mmol) in 0.5 mL of pyridine at room temperature was added 4-dimethylaminopyridine (2.0 mg, 0.014 mmol) followed by Ac$_2$O (0.01 mL, 0.1 mmol). After stirring at room temperature for 21 h, the solution was diluted with 10 mL of EtOAc, and poured into 20 mL of a saturated aqueous NaHCO$_3$ solution. The organic layer was separated, and the aqueous layer was extracted with EtOAc (20 mL, 3 times). The organic layers were combined and dried over Na$_2$SO$_4$. Removal of the solvent followed by flash chromatography purification (5% EtOAc/hexane) gave the desired bis-acetate 23 (3.4 mg, 60% yield) as a colorless oil.

23: $^1$H NMR (500 MHz, CDCl$_3$): δ (ppm) 0.518 (q, J=8.0, 1.0 Hz, 6H, TES CH$_2$) 0.600 (qd, J=8.0, 5.0 Hz, 6H, TES CH$_2$), 0.912 (t, J=8.0 Hz, 9H, TES CH$_3$), 0.951 (t, J=8.0 Hz, 9H, TES CH$_3$), 1.042 (s, 3H, Me17), 1.109 (s, 3H, Me16), 1.484 (m, 1H, H14α), 1.653 (s, 3H, Me19), 1.918(ddd, J=14.0, 10.5, 2.5 Hz, 1H, H6β), 2.107 (d, J=1.0 Hz, 3H, Me18), 2.138 (s, 3H, OAc10), 2.162–2.207 (m, 2H, H1, H14β), 2.538 (m, 1H, H6α), 2.626 (s, 3H, OAc4), 3.628 (d, J=6.5 Hz, 1H, H3), 3.999 (dd, J=6.5, 2.5 Hz, 1H, H2), 4.496 (d, J=12.0 Hz, 1H, 1H×BOM), 4.538 (d, J=8.5 Hz, 1H, H20β), 4.578–4.627 (m, 3H, H7α, H20α, 1H×BOM), 4.652 (d, J=6.5 Hz, 1H, 1H×BOM), 4.709 (m, 1H, H13β), 4.733 (d, J=6.5 Hz, 1H, 1H×BOM), 4.943 (dd, J=9.5, 2.5 Hz, 1H, H5β), 6.394 (s, 1H, H10), 7.284–7.369 (m, 5H, 5H×BOM).

1-Deoxy-baccatin III. To a solution of bis-acetate 23 (3.4 mg, 0.0042 mmol) in 0.5 mL of EtOAc and 0.5 mL of t-BuOH at room temperature was added 4.0 mg of 10% Pd on carbon. After stirring under H$_2$ for 45 min., the mixture was diluted with 10 mL of EtOAc, and filtered through a short pad of celite. Removal of the solution gave a colorless oil, which was then dissolved in 0.5 mL of CHCl$_3$, and loaded onto a column (silica gel). After 2 h at room temperature, the column was washed with EtOAc. Removal of the solvent then gave the desired crude product, which was used without any further purification.

To a solution of the above crude product in 0.5 mL of pyridine at room temperature was added 4-pyrrolidino-pyridine (1.8 mg, 0.012 mmol) followed by 0.5 mL (0.5 mmol) of a 1.0 M solution of BzCl in pyridine (0.5 mL). After stirring at room temperature for 26 h, the solution was diluted with 10 mL of EtOAc, and poured into 20 mL of a saturated aqueous NaHCO$_3$ solution. The organic layer was separated, and the aqueous layer was extracted with EtOAc (20 mL, 3 times). The organic layers were combined and dried over Na$_2$SO$_4$. Removal of the solvent then gave the crude benzoate, which was used without any further purification.

To a solution of the above crude benzoate in 0.1 mL of CH$_3$CN at room temperature was added 0.5 mL of a 48% HF/pyridine/CH$_3$CN (1:3.5:3.5) solution. After stirring at room temperature for 27 h, the solution was diluted with 10 mL of EtOAc, and poured into 20 mL of a saturated aqueous NaHCO$_3$ solution. The organic layer was separated, and the aqueous layer was extracted with EtOAc (10 mL, 3 times). The organic layers were combined and dried over Na$_2$SO$_4$. Removal of the solvent followed by flash chromatography purification (60% EtOAc/hexane) gave the desired 1-deoxy-baccatin III (1.4 mg, 59% overall yield from bis-acetate 23).

1-Deoxy-baccatin III: $^1$H NMR (500 MHz, CDCl$_3$): δ (ppm) 1.069 (s, 3H, Me17), 1.204 (s, 3H, Me16), 1.667 (s, 3H, Me19), 1.730 (ddd, J=15.0, 7.5, 1.0 Hz, 1H, H14α), 1.890 (ddd, J=15.0, 6.0, 2.0 Hz, 1H, H6β), 1.978 (d, J=5.5 Hz, 1H, OH13), 2.034 (ddd, J=9.0, 3.5, 1.0 Hz, 1H, H1), 2.085 (d, J=1.0 Hz, 3H, Me18), 2.227 (s, 3H, OAc10), 2.290 (s, 3H, OAc4), 2.387 (d, J=4.5 Hz, 1H, OH7), 2.516 (ddd, J=15.0, 10.0, 9.0 Hz, 1H, H14β), 2.583 (ddd, J=15.0, 10.0, 7.0 Hz, 1H, H6α), 3.738 (d, J=6.5 Hz, 1H, H3α), 4.156 (dd, J=8.5, 1.0 Hz, 1H, H20β), 4.373 (d, J=8.5 Hz, 1H, H20α), 4.471 (ddd, J=10.0, 7.0, 4.5 Hz, 1H, H7α), 4.712 (dddd, J=10.0, 7.5, 5.5, 1.0 Hz, 1H, H13β), 5.023 (ddd, J=9.5, 2.0, 1.0 Hz, 1H, H5α), 5.643 (dd, J=6.5, 3.5 Hz, 1H, H2β), 6.320 (s, 1H, H10α), 7.472 (t, J=8.0 Hz, 2H, benzoate-m), 7.597 (dd, J=8.0, 1.0 Hz, 1H, benzoate-p), 8.085 (dd, J=8.0, 1.0 Hz, 2H, benzoate-o).

In view of the above, it will be seen that the several objects of the invention are achieved.

As various changes could be made in the above compositions without departing from the scope of the invention, it is intended that all matter contained in the above description be interpreted as illustrative and not in a limiting sense.

What we claim is:

1. A compound selected from the group consisting of:

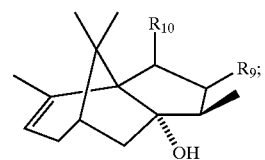

(a)

wherein R$_9$ is hydroxy or protected hydroxy; and R$_{10}$ is keto;

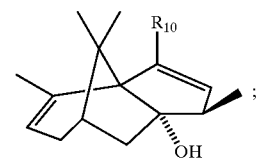

(b)

wherein R$_{10}$ is hydroxy or protected hydroxy;

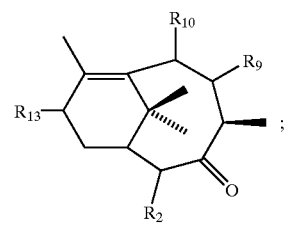

(c)

wherein $R_2$ is hydroxy or protected hydroxy; $R_9$ is hydroxy or protected hydroxy; $R_{10}$ is hydroxy or protected hydroxy; and $R_{13}$ is hydroxy or protected hydroxy;

(d)

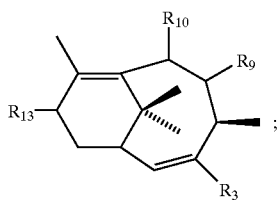

wherein $R_3$ is hydroxy or protected hydroxy; $R_9$ is hydroxy or protected hydroxy; $R_{10}$ is hydroxy or protected hydroxy; and $R_{13}$ is hydroxy or protected hydroxy;

(e)

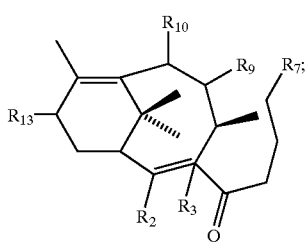

wherein $R_2$ is hydroxy or protected hydroxy, or together with $R_3$ forms a carbonate; $R_3$ is hydrogen, hydroxy or protected hydroxy, or together with $R_2$ forms a carbonate; $R_7$ is hydroxy, protected hydroxy or keto; $R_9$ is hydroxy, protected hydroxy or keto; $R_{10}$ is hydroxy or protected hydroxy; and $R_{13}$ is hydroxy or protected hydroxy;

(f)

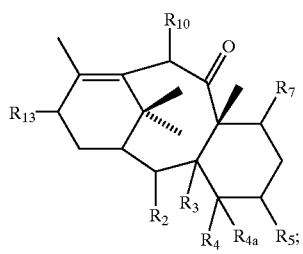

wherein $R_2$ is hydroxy or protected hydroxy; $R_4$ is hydroxy or protected hydroxy, or together with $R_{4a}$ forms a keto; $R_{4a}$ is —CH$_2$OH or together with $R_4$ forms a keto; $R_5$ is hydroxy, protected hydroxy or CH$_3$SO$_2$—; $R_7$ is hydroxy or protected hydroxy; $R_{10}$ is hydroxy or protected hydroxy; and $R_{13}$ is hydroxy or protected hydroxy; and (g)

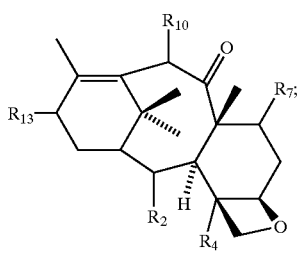

wherein $R_2$ is hydroxy or protected hydroxy; $R_4$ is hydroxy, protected hydroxy or acetoxy; $R_7$ is protected hydroxy; $R_{10}$ is hydroxy, protected hydroxy or acetoxy; and $R_{13}$ is hydroxy or protected hydroxy.

2. A process for the preparation of an intermediate useful in the synthesis of 1-deoxy baccatin III, 1-deoxy taxol or 1-deoxy taxol analogs comprising at least one of the following steps:

(a) reacting a compound having the formula:

[9]

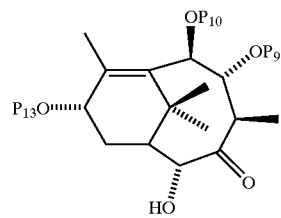

with a vinyl organometallic reagent to form the intermediate compound having the formula:

[10]

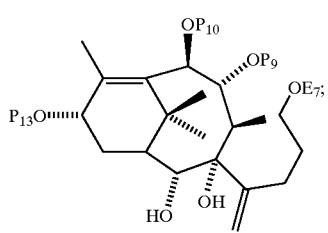

(b) reacting a compound having the formula:

[14]

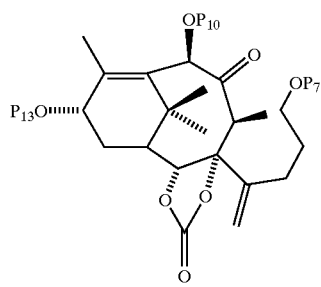

with a paladium catalyst to form the intermediate compound having the formula:

[15]

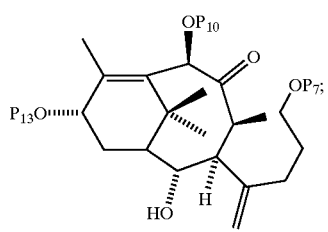

(c) reacting a compound having the formula:
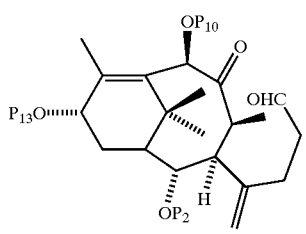
[17]
with a base, and protecting the C7 hydroxy substituent, to form a compound having the formula:
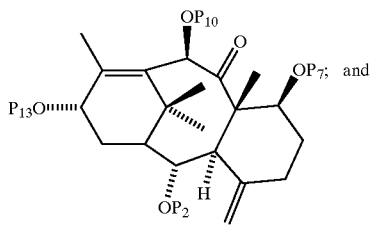
[18]
and
(d) reacting a compound having the formula:
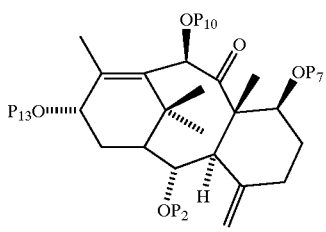
[18]
with $SeO_2$ to form the intermediate compound having the formula:
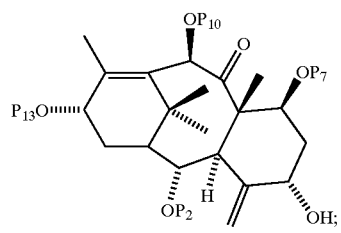
[19]
wherein $E_7$ is hydrogen or a hydroxy protecting group, and $P_2$, $P_7$, $P_9$, $P_{10}$ and $P_{13}$ are hydroxy protecting groups.
* * * * *

UNITED STATES PATENT AND TRADEMARK OFFICE
CERTIFICATE OF CORRECTION

PATENT NO.    : 6,620,950 B2
DATED         : September 16, 2003
INVENTOR(S)   : Robert A. Holton et al.

It is certified that error appears in the above-identified patent and that said Letters Patent is hereby corrected as shown below:

Column 7,
Lines 17-27, chemical structure [12] should read:

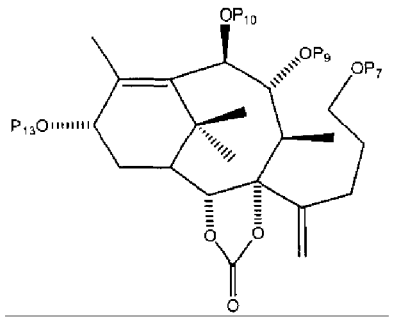

Lines 32-43, chemical structure [13] should read:

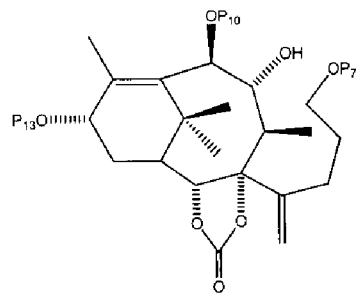

Columns 27 and 28,
Reaction Scheme 12, after the second recited structure, remove the

UNITED STATES PATENT AND TRADEMARK OFFICE
CERTIFICATE OF CORRECTION

PATENT NO. : 6,620,950 B2
DATED : September 16, 2003
INVENTOR(S) : Robert A. Holton et al.

It is certified that error appears in the above-identified patent and that said Letters Patent is hereby corrected as shown below:

Column 40,
Line 9, "5BxBOM." should read -- 5HxBOM). --.

Column 43,
Lines 19-27, chemical structure (e) should read:

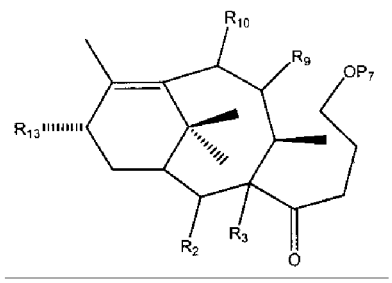

Signed and Sealed this

Twenty-eighth Day of June, 2005

JON W. DUDAS
*Director of the United States Patent and Trademark Office*